(12) United States Patent
Adamczyk et al.

(10) Patent No.: US 6,472,227 B1
(45) Date of Patent: Oct. 29, 2002

(54) BARBITURATE ASSAY, TRACERS, IMMUNOGENS, ANTIBODIES AND KIT

(75) Inventors: Maciej Adamczyk, Gurnee; Luis A. Cantarero, Mundelein; Robert Edward Dubler, Gurnee; Jonathan Grote, Grayslake; Patrick J. Jonas, Waukegan; Jane Ann Nelson, Palatine, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 08/033,075

(22) Filed: Mar. 10, 1993

Related U.S. Application Data

(63) Continuation of application No. 07/524,195, filed on May 16, 1990, now abandoned, which is a continuation-in-part of application No. 07/284,781, filed on Dec. 12, 1988, now abandoned, which is a continuation-in-part of application No. 06/870,671, filed on Jun. 4, 1986, now abandoned.

(51) Int. Cl.[7] ............................................. G01N 33/533
(52) U.S. Cl. ........................ 436/546; 436/537; 436/800; 436/816
(58) Field of Search ................................. 436/546, 547, 436/548, 436, 537, 538, 800, 816

(56) References Cited

U.S. PATENT DOCUMENTS

| 4,107,157 A | * | 8/1978 | Spector ..................... 530/387 |
| 4,151,268 A | | 4/1979 | Spector ..................... 436/542 |
| 4,244,939 A | | 1/1981 | Parsons, Jr. et al. ........ 436/542 |
| 4,340,736 A | | 7/1982 | Focella et al. .............. 544/301 |
| 4,510,251 A | * | 4/1985 | Kirkemo et al. ............. 436/536 |
| 4,939,264 A | * | 7/1990 | Heiman et al. .............. 436/537 |

FOREIGN PATENT DOCUMENTS

| EP | 0 110 186 A1 | 11/1983 |
| EP | 0 199 963 A1 | 3/1986 |
| EP | 0 218 010 A2 | 6/1986 |

OTHER PUBLICATIONS

Clinical Chemistry, vol. 30, No. 11, Nov. 1984, Winston US pp. 1765–1769; D.L. Colbert Et Al.: "Single–reagent polarization fluoroimmunassay for barbiturates in urine".

Clinical Chemistry, vol. 28, No. 11, Nov. 1982, Winston US pp. 2278–2282; M. Lu–Steffes Et Al.: "Fluorescence polarization immunoassay IV. Determination of phenytoin and phenobarbital in human serum and plasma".

\* cited by examiner

*Primary Examiner*—Donna C. Wortman
(74) *Attorney, Agent, or Firm*—Regina M. Anderson

(57) ABSTRACT

The present invention is directed to a fluorescence polarization immunoassay for barbiturates, to the various components needed for preparing and carrying out such an assay, and to methods of making these components. Specifically, tracers, immunogens and antibodies are disclosed, as well as methods for preparing them and a reagent kit containing them. The tracers and the immunogens are made from substituted barbiturate compounds. A fluorescein moiety is included in the tracer, while a poly(amino acid) forms a part of the immunogen. The assay is conducted by measuring the degree of polarization retention of plane—polarized light that has been passed through a sample containing antiserum and tracer.

2 Claims, 8 Drawing Sheets

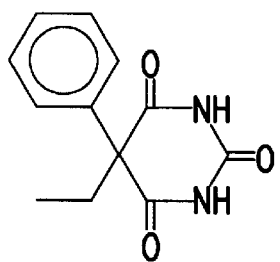
FIG. 1-1
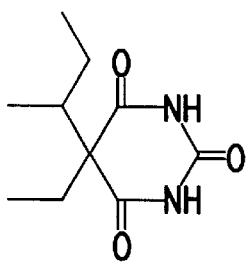
FIG. 1-2
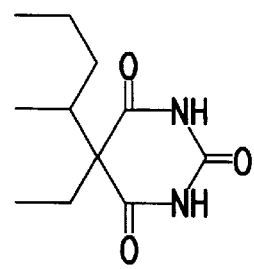
FIG. 1-3
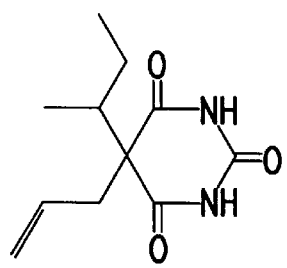
FIG. 1-4
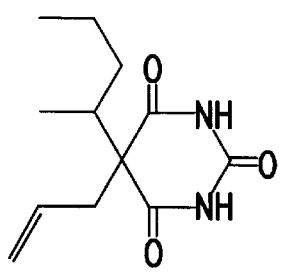
FIG. 1-5
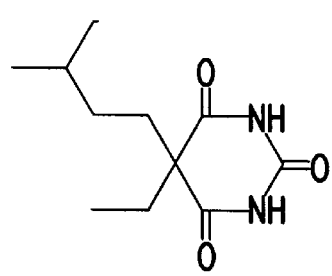
FIG. 1-6
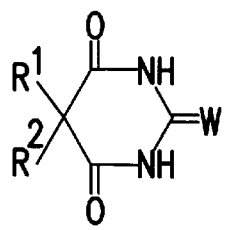
FIG. 2
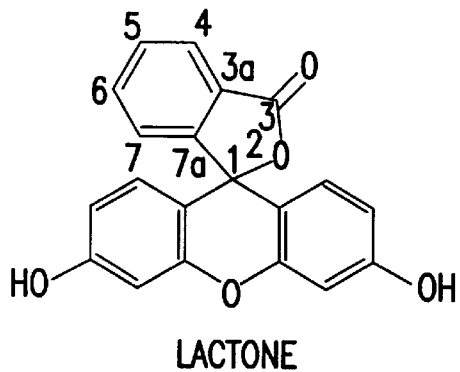
LACTONE
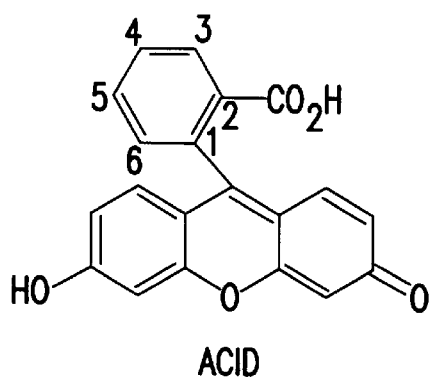
ACID
FIG. 3

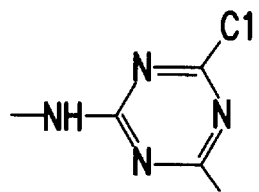
FIG. 4-1
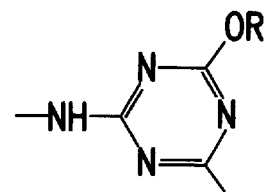
FIG. 4-2
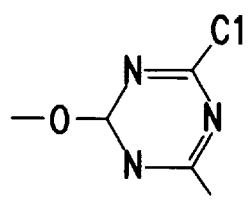
FIG. 4-3
—NH—
FIG. 4-4
—CO—
FIG. 4-5
—C(NH)—
FIG. 4-6
—NH—CO—
FIG. 4-7
—NH—CS—
FIG. 4-8
—O—CO—
FIG. 4-9
—O—CS—
FIG. 4-10
—SO$_2$—
FIG. 4-11
—O—CO—NH—SO$_2$—
FIG. 4-12

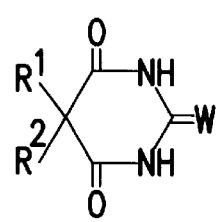 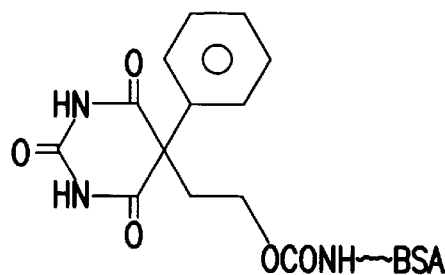
FIG. 27    FIG. 28
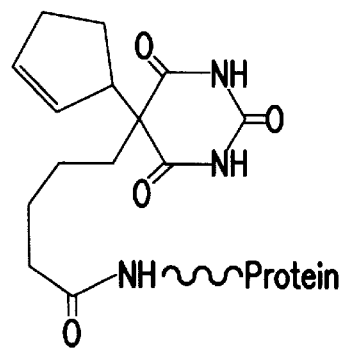 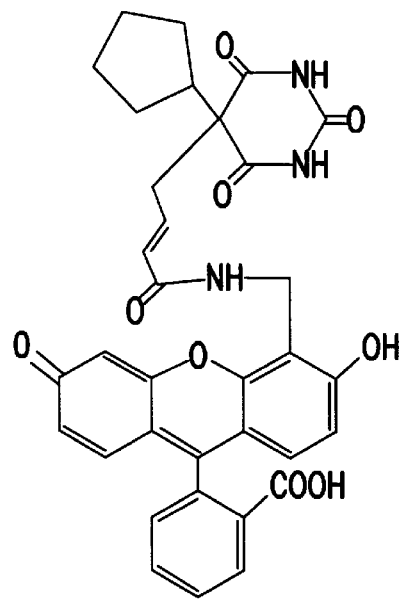
FIG. 29    FIG. 30
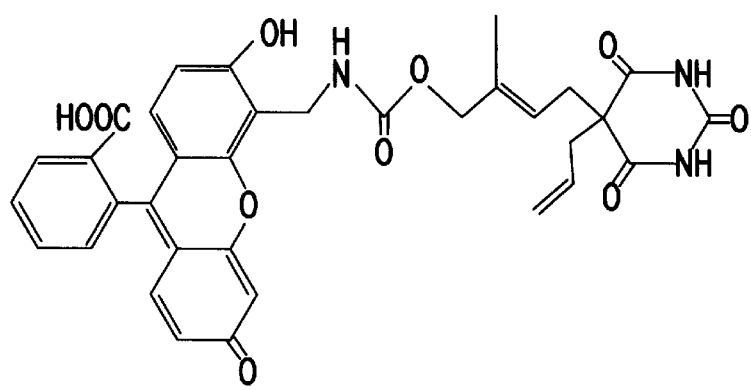
FIG. 31

BARBITURATE ASSAY, TRACERS, IMMUNOGENS, ANTIBODIES AND KIT

This application is a continuation of Ser. No. 07/524,195, filed May, 16, 1990, now abandoned, which was a continuation-in-part of Ser. No. 07/284,781, filed Dec. 12, 1988, now abandoned, which was a continuation-in-part of Ser. No. 06/870,671, filed Jun. 4, 1986, now abandoned.

BACKGROUND OF THE INVENTION

1. Technical Field

The present invention relates to a method and reagents for a fluorescence polarization immunoassay procedure for determining the amount of barbiturate in fluids, especially biological fluids such as serum, plasma or urine, and to a method of making the reagents. More specifically, the invention relates to (1) reagents (tracers and antibodies, and a kit containing the same) for determining the amount of barbiturate in a sample; (2) immunogen compounds used to raise antibodies; (3) synthetic methods (for making the tracer and immunogen compounds); and (4) analytical methods for conducting the assay.

2. Background Art

Barbiturates are central nervous system depressants. Therapeutically, they are used as sedatives, hypnotics and anticonvulsants. Although the legal availability of barbiturates has declined, they are frequently abused sedative or hypnotic drugs and are commonly used to commit suicide.

The physiological absorption, action and toxicity of barbiturates vary widely and are dependent on the nature of the 5-substituted groups and imino-hydrogens. Approximately 35% of the barbiturate in blood is plasma protein bound. Barbiturates are distributed in various tissues and organs. Barbiturates are primarily metabolized in the liver and, with a few exceptions, are generally excreted in urine mainly as nonactive metabolites.

The most commonly abused barbiturates are the short to medium acting: secobarbital, pentobarbital, amobarbital, etc. These are widely used to reduce excitation states due to the use of stimulants. Tolerance to these drugs can develop from chronic use, and death may occur from either overdose or abrupt withdrawal of the drug.

In the past, barbiturate levels in urine have typically been measured by high performance liquid chromatography (HPLC), gas chromatography (GC), enzyme immunoassay (EIA), substrate-linked fluorescence immunoassay (SLFIA) and radioimmunoassay (RIA). These methods are reasonably specific for detecting drug levels; however, they are not without drawbacks. HPLC and GC methods require sample extraction procedures and the assay time is lengthy. Both EIA and SLFIA involve enzyme reactions and have the following disadvantages:

1) the reagents are relatively unstable; 2) any components in the biological samples which may influence the enzyme reaction in EIA or SLFIA (such as enzyme inhibitors or enzymes which catalyze similar reactions) will affect the assay results; and 3) EIA and SLFIA measure either absorbance or fluorescence, and any compounds in the biological samples which may affect absorbance or fluorescence (such as lipid, hemoglobin, bilirubin or other chromophores or fluorophores) will affect the accuracy of the results obtained from these assays. RIA reagents have the following shortcomings: 1) short shelf-life; 2) radiation hazards; and 3) problems associated with the storage and disposal of radioactive materials.

Typically, competitive binding immunoassay are used for measuring ligands in a test sample. (For purposes of this disclosure, a "ligand" is a substance of biological interest to be determined quantitatively by a competitive binding immunoassay technique.) The ligands compete with a labeled reagent, or "ligand analog," or "tracer," for a limited number of binding sites on antibodies specific to the ligand and ligand analog. The concentration of ligand in the sample determines the amount of ligand analog which binds to the antibody: the amount of ligand analog that will bind is inversely proportional to the concentration of ligand in the sample, because the ligand and the ligand analog each bind to the antibody in proportion to their respective concentrations.

Fluorescence polarization provides a quantitative means for measuring the amount of tracer-antibody conjugate produced in a competitive binding immunoassay. Fluorescence polarization techniques are based on the principle that a fluorescent labeled compound, when excited by plane-polarized light, will emit fluorescence having a degree of polarization inversely related to its rate of molecular rotation.

Accordingly, when a tracer-antibody conjugate having a fluorescent label is excited with plane-polarized light, the emitted light remains highly polarized because the fluorophore is constrained by the antibody from rotating between time that light is absorbed and emitted. In contrast, when an unbound tracer is excited by plane-polarized light, its rotation is much faster than that of the corresponding tracer-antibody conjugate. As a result, the light emitted from the unbound tracer molecules is depolarized.

A problem that heretofore has prevented the accurate determination of barbiturates and other "drugs of abuse" in urine by fluorescence polarization techniques is that of riboflavin interference. Riboflavin, or vitamin $B_2$, is a common constituent of many foods and of commercially available vitamin supplements. Riboflavin is excreted primarily in the urine and has a fluorescence spectrum quite similar to that of fluorescein. As a result, the presence of riboflavin in even moderate amounts in urine samples creates an interference which can produce erroneous results. While ordinary consumption of riboflavin is unlikely to produce more than trace amounts of riboflavin in the urine, test results can readily be distorted by the consumption of excessive quantities of vitamin supplements by persons wishing to prevent detection of barbiturate use.

The present invention is characterized by a more uniform cross-reactivity for the commonly used barbiturates. Further, this invention offers an advance in the art, in that tracers, a method for making the tracers, and an assay using the tracers, are provided specifically for the determination of barbiturates without riboflavin interference.

SUMMARY OF THE INVENTION

The present invention is directed to a fluorescence polarization assay for barbiturates; to tracers, immunogens and antibodies for use in the assay; to a reagent kit; and to methods for making the tracers, immunogens and antibodies, A first aspect of the invention relates to the discovery of unique tracers and immunogens having novel structures. According to the first aspect of the invention, the tracers and the immunogens are represented by the structural formulas shown in FIG. 27 and FIG. 2, respectively, wherein, for the tracers:

(1) W is oxygen or sulfur;
(2) $R^1$ is an alkyl, alkenyl, aryl, or alkynyl group having a total of from 1 to 12 carbon atoms, and including from 0 to 1 halogen atoms, arranged in a straight or branched chain, and including up to one aliphatic or aromatic ring structure;
(3) $R^3$ is $R^4Fl$;
(4) Fl is fluorescein or a fluorescein derivative; and
(5) $R^4$ is a linking group which:
  (a) has a total of from 0 to 15 carbon atoms and heteroatoms, arranged in a straight or branched chain, and includes up to one aliphatic or aromatic ring structure, said heteroatoms being O, N, S, P or F; and
  (b) has a total of from 0 to 5 heteroatoms;

and, for the immunogens:
(1) W is oxygen or sulfur;
(2) $R^1$ is an alkyl, alkenyl, aryl, or alkynyl group having a total of from 1 to 12 carbon atoms, including from 0 to 1 halogen atoms, and including up to one aliphatic or aromatic ring structure;
(3) $R^2$ is R—Q;
(4) Q is a poly(amino acid), a poly(amino acid) derivative or another immunogenically active carrier; and
(5) R is a linking group which:
  (a) has a —$CH_2$—, a —CH=, a

or a —NH— at that end of said linking group which is linked to Q;
  (b) has a total of from 0 to 20 carbon atoms and heteroatoms, arranged in a straight or branched chain, and includes up to one aliphatic or aromatic ring structure, said heteroatoms being O, N, S, P or F; and
  (c) has a total of from 0 to 7 heteroatoms.

A second aspect of the invention relates to monoclonal or polyclonal antibodies prepared against the novel immunogen. According to the second aspect of the invention, antibodies are prepared in response to a compound according to FIG. 2. The most preferred antibodies of the present invention are prepared in response to the novel immunogen shown in FIG. 29.

According to a third aspect of the invention, an immunogen may be synthesized by a method comprising the step of coupling a compound represented by the structural formula shown in FIG. 2 wherein:

W is oxygen or sulfur;
$R_1$ is alkyl, alkenyl, aryl or alkynyl having a total of from 1 to 12 carbon atoms, arranged in a straight or branched chain, and containing up to one aliphatic or aromatic ring structure;

$R_2$ is CH —R—X;
X is $NH_2$, Cl, Br, I, OH, $CO_2H$, O—C—Cl,

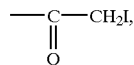

—CHO,

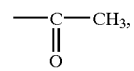

or

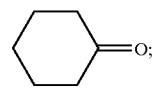

and
R is a linking group including up to 7 heteroatoms and having a total of from 0 to 20 carbon atoms and heteroatoms arranged in a straight or branched chain and containing up to one aliphatic or aromatic ring structure;

with a poly(amino acid), a poly(amino acid) derivative or another immunologically active carrier.

According to a fourth aspect of the invention, a method is provided for making a tracer by coupling a compound represented by the structural formula shown in FIG. 27, wherein;

W is oxygen or sulfur;
$R^1$ is alkyl, alkenyl or alkynyl having a total of from 1 to 12 carbon atoms arranged in a straight or branched chain and containing up to one aliphatic or aromatic ring structure;
$R^3$ is $CH_2$—R—Y;
Y is —$NH_2$, COOH, —COCl, $SO_3H$; $SO_2Cl$, SH, CHO, CN, OH, or I; and
R is a linking group including up to 10 heteroatoms, having a total of from 0 to 20 carbon atoms and heteroatoms, arranged in a straight or branched chain and containing up to one aliphatic or aromatic ring structure;

with fluorescein or a derivative of fluorescein.

Preferably, the tracer is prepared by coupling a precursor of the structural formula shown in FIG. 27 wherein:

W and $R^3$ are as defined above;
$R^1$ is alkyl having 4 or 5 carbon atoms arranged in a branched chain and containing no ring structure;
Y is $NH_2$ or COOH; and
R is a linking group including up to 3 heteroatoms, having a total of from 3 to 5 carbon atoms and heteroatoms arranged in a straight or branched chain and containing no ring structure.

Preferred derivatives of fluorescein include amino, amido, amidino, urea, thiourea, carbamido, thiocarbamido or triazinylamino derivatives. Most preferred at the present time are the amino derivatives, particularly aminomethylfluorescein.

A fifth aspect of the invention relates to the elimination of potential fluorescence interference by riboflavin. Riboflavin binding protein (RBP) is added either directly to each sample or to one or more of the reagents utilized in the assay, wherein it binds all riboflavin present into RBP-riboflavin complexes, thus eliminating fluorescence interference. Other fluorescence-quenching substances may also be utilized for this purpose.

According to a sixth aspect of the invention, a process for detecting or measuring the concentration of barbiturates is provided. A sample is contacted with barbiturate antiserum, and a fluorescein-containing barbiturate derivative capable of producing a detectable fluorescence polarization response to the presence of the barbiturate antiserum. Plane-polarized light is then passed through the solution to obtain a fluorescence polarization response, and this response is detected as a measure of the amount of barbiturate in the sample.

A seventh aspect of the present invention relates to a stabilized reagent kit which is useful for detecting commonly-used barbiturates in a single assay. The reagent kit contains novel tracers, and salts thereof, which are useful as reagents in the novel method of the present invention. Other components of the reagent kit in accordance with the instant invention include a solution containing an amount of riboflavin binding protein which is effective to reduce fluorescence interference by riboflavin and an antibody reagent which has been raised against an immunogen which is capable of specifically recognizing and binding the commonly-used barbiturates and the novel tracer reagents of the present invention.

Further objects and attendant advantages of the invention will be best understood from a reading of the following detailed description taken together with the Figures and the Examples.

BRIEF DESCRIPTION OF THE DRAWINGS

In the following Figures the symbol "Fl" represents a fluorescein moiety, and the various other symbols are noted in the Detailed Description of the Invention.

FIG. 1 shows the general structure of some of the barbiturates to be semi-quantitatively determined in accordance with the present invention.

FIG. 2 shows a general structural formula for the immunogens of the present invention, as well as for the classes of reactants used in preparing them.

FIG. 3 shows the alternate structural formula and names of the fluorescein moiety included in the tracers of the present invention.

FIG. 4 shows various linkages that couple the fluorescein moiety to the precursor in FIG. 2, when FIG. 2 represents a precursor for the tracers.

FIG. 27 shows a general structural formula for the tracers of the present invention, as well as the classes of reactants used in preparing them.

FIG. 28 shows a preferred immunogen of the present invention.

FIG. 29 shows the most preferred immunogen of the present invention.

FIG. 30 shows the most preferred tracer of the present invention.

FIG. 31 shows a preferred tracer of the present invention.

DETAILED DESCRIPTION OF THE INVENTION

Figure 5:
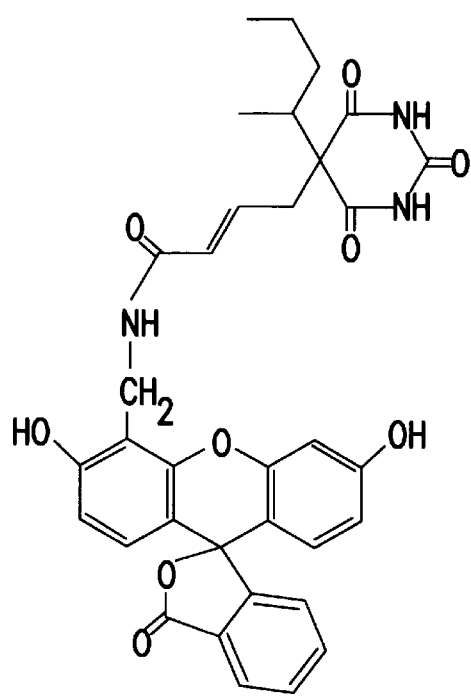
FIGS. 5 through 19 show various examples of structures of tracers in accordance with the present invention.
Figure 6:
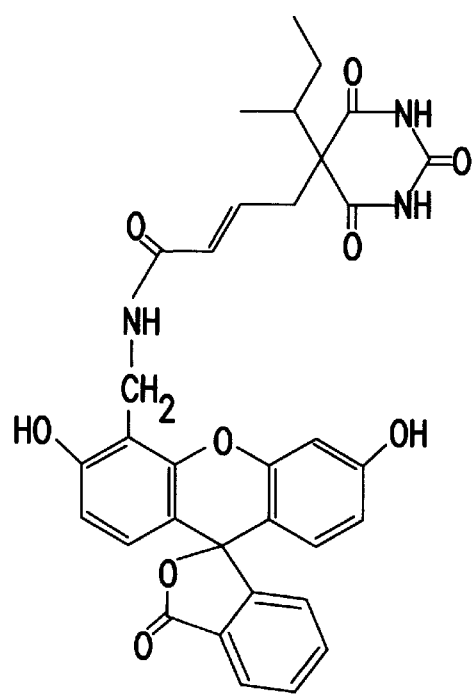
Figure 7:
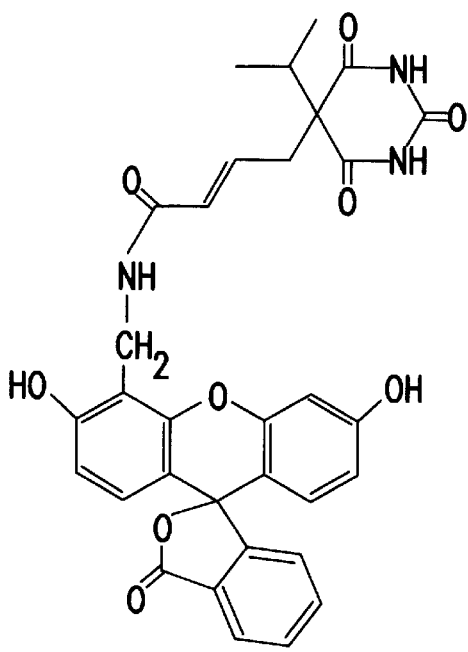
Figure 8:
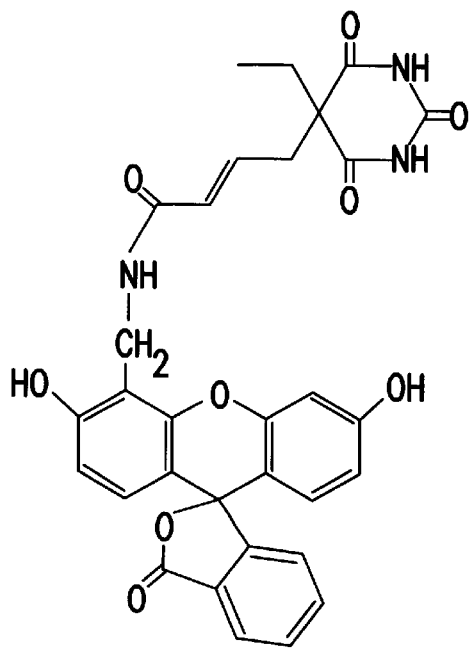
Figure 9:
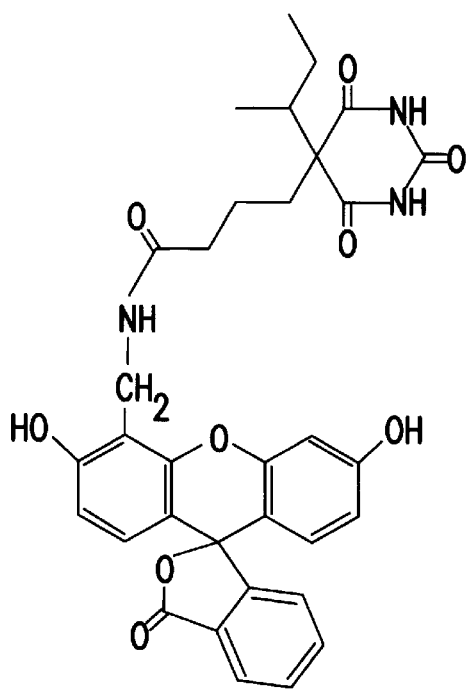
Figure 10:
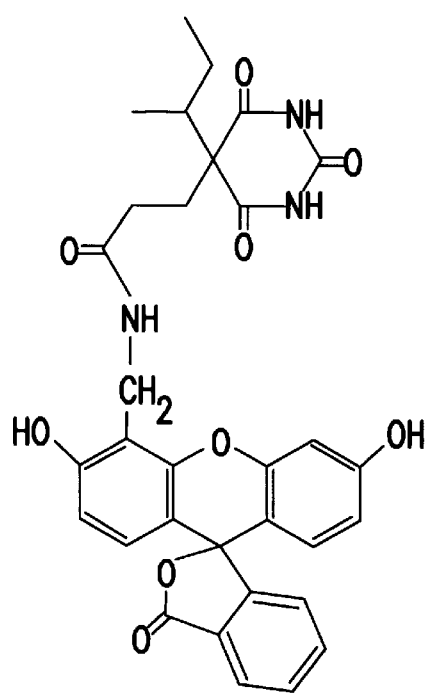
Figure 11:
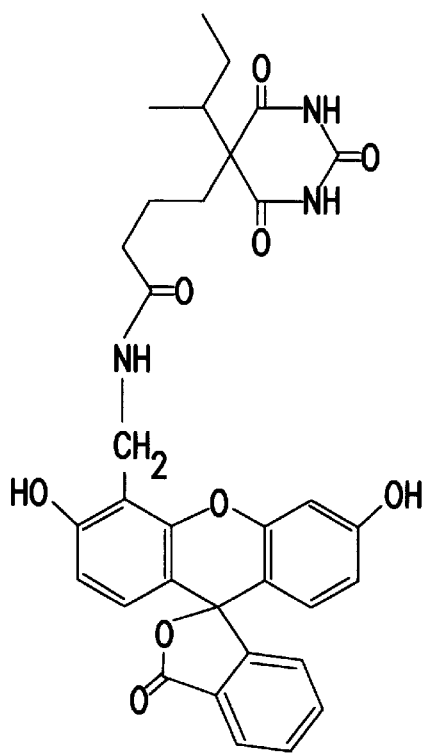
Figure 12:
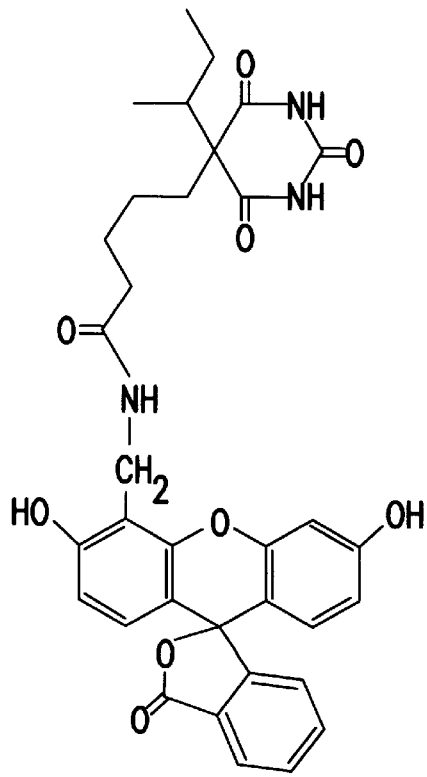
Figure 13:
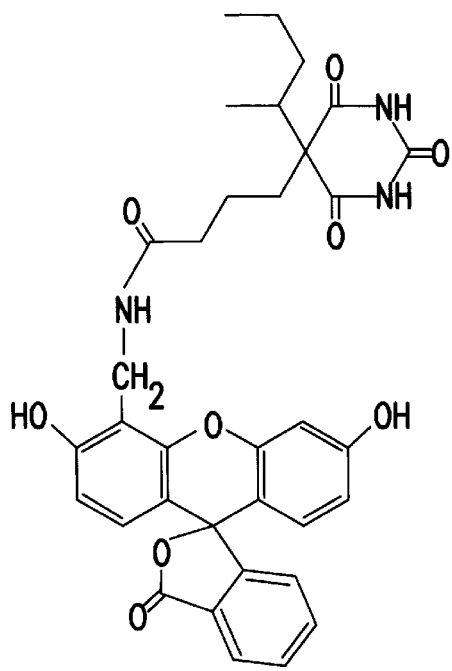
Figure 14:
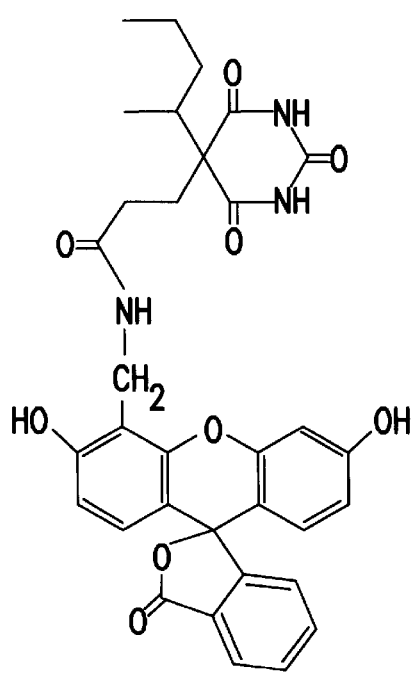
Figure 15:
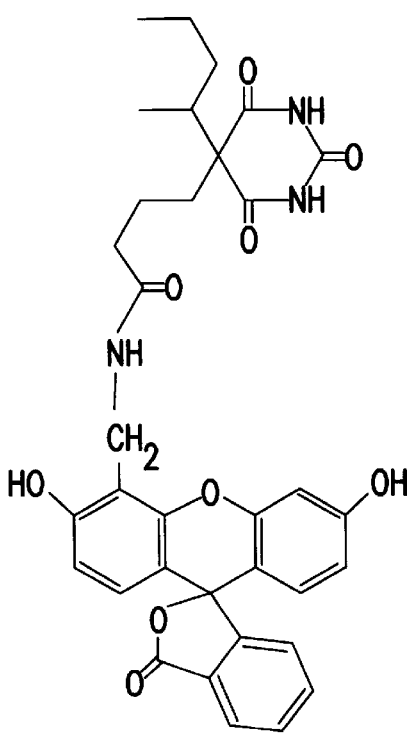
Figure 16:
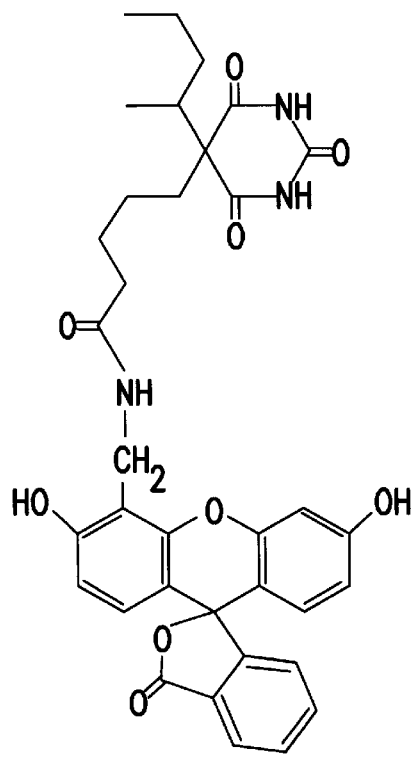
Figure 17:
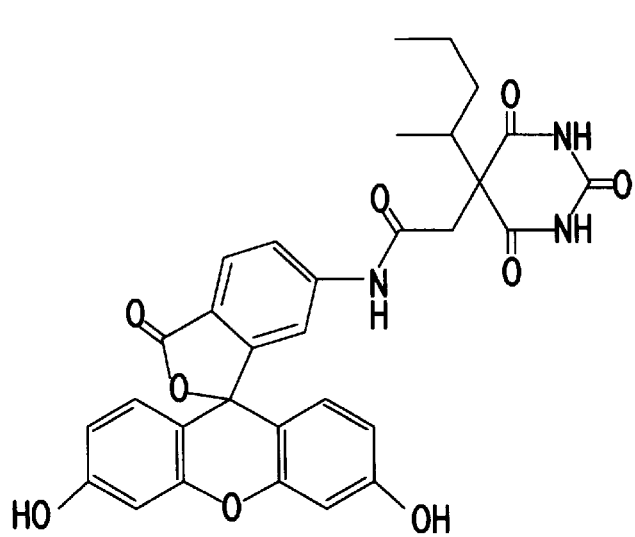
Figure 18:
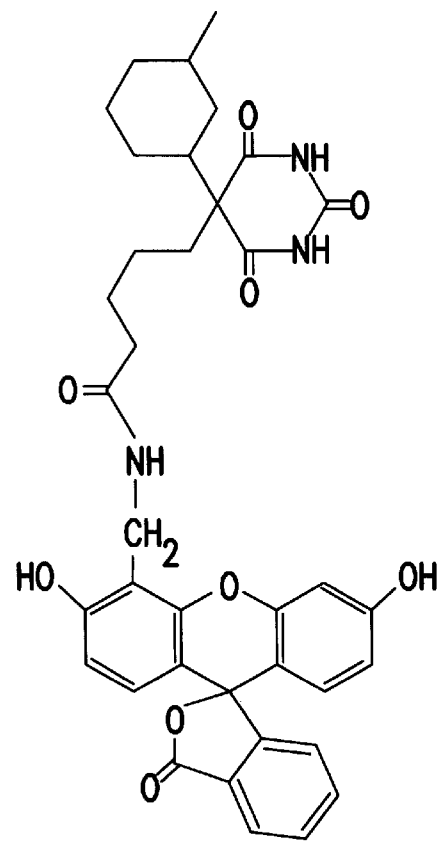
Figure 19:
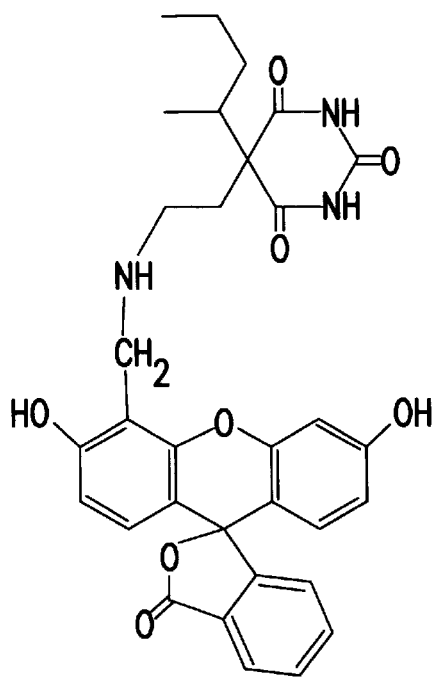
Figure 20:
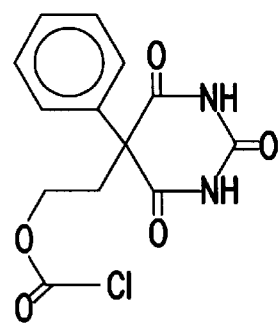
FIGS. 20 through 26 show various examples of structures of hapten reactants used to form the immunogens employed in the present invention.

The various aspects of the invention will now be discussed in detail in relation to the Figures.

The present invention involves the use of fluorescein and derivatives of fluorescein. In particular, a necessary property of fluorescein and its derivatives for the usefulness of the tracer compounds of the present invention is the fluorescence of fluorescein. Fluorescein exists in two tautomeric forms, illustrated in FIG. 3, depending on the acid concentration (pH) of the environment. In the open (acid) form, there are a number of conjugated double bonds which make that form of fluorescein (and compounds containing a fluorescein moiety) capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, allowing the compounds to exist in the open, fluorescent form when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

The numbering of carbon atoms of the fluorescein molecule varies, depending upon whether the open or closed form of the molecule is considered.

Accordingly, the literature concerning fluorescein and its compounds is not uniform as to carbon atom numbering. In the closed form, the para-carbon to the carbonyl of the lactone on the phenyl ring is numbered 6. In the open form, the para-carbon to the carboxylic acid group on the phenyl ring is numbered 5 (see FIG. 3). In this disclosure the numbering of the closed form is adopted because the raw materials used in the syntheses are most popularly numbered with that system. The carbon atom of fluorescein and its compounds which is opposite the carboxyl group is therefore numbered "6" for purposes of the present disclosure.

A tracer in solution which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule, which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free tracer, i.e., low. If the test sample contains a low concentration of the ligand, the polarization value is closer to that of the bound tracer, i.e., high. By sequentially exciting the reaction mixture of an immunoassay with vertically and then horizontally polarized light and analyzing only the vertical component of the emitted light, the polarization of fluorescence in the reaction mixture may be accurately determined. The precise relationship between polarization and concentration of the ligand to be determined is established by measuring the polarization values of calibrators with known concentrations of ligand. The concentration of the ligand in a sample can be extrapolated from a standard curve prepared in this manner.

The particular antibodies and tracers formed in accordance with this invention have been found to produce very good assays.

Prior to the invention described herein, the problem of developing an immunologically-based diagnostic test with broad barbiturate specificity (i.e. lack of specificity or a more uniform cross-reactivity of the antibody which is employed in the immunoassay, and which is specific to the ligand and tracer, for the commonly-used barbiturates, such as those shown in FIG. 1) was solved by mixing several antisera, each specific for one barbiturate, with a patient sample. This mixing of antibodies with differing barbiturate specificities would result in an assay having the significant disadvantages of a lower sensitivity, poor cross reactivity, and a broad variability from lot to lot of antiserum blend.

The invention described herein solved the above-described problems. It was surprisingly found that an immunologically-based diagnostic test with broad barbituric specificity could be developed when monoclonal or polyclonal antibodies which had been raised against only one barbituric structure were employed in an immunocompetitive environment in an appropriate combination with tracers (fluorescent-labeled barbiturate derivatives). The optimum combination was found to have been an immunogen and a tracer containing five-membered ring structures. In the assay of the present invention, this broad barbiturate specificity was achieved by designing a tracer and the immunogens employed to generate the antibodies contained in antiserum in such a manner that: (1) the tracers and the immunogens both have chemical structures which are similar to commonly-used barbiturates; and (2) the antibodies contained in the antiserum are cross-reactive rather than specific for the tracer, and therefore bind with less affinity to the tracer, such that the binding of the antibodies to the tracer is allowed to be displaced. The various barbiturates in the sample will have the ability to similarly displace the tracer from the antibody, which results in a more equivalent detection system for the various commonly-used barbiturates. Which combination of antibody and tracer would result in an immunologically-based diagnostic test with broad barbituric specificity was completely unpredictable. Thus, the favorable results which were obtained from certain experiments involving such combinations, and not others, were, thus, completely unexpected.

Consequently, the method of the present invention differs significantly from related technology described in the art in that the polyspecificity of the immunological reagents of the immunoassay is generally achieved by using two different barbiturate derivatives to generate the two crucial immunological reagents of the assay, the tracer and the antibody. It provides for a more equivalent barbiturate detection system in that it has the unusual capability of responding more similarly to a broad range of barbiturates. In addition, it overcomes the uncertainty of the assays described in the art with respect to the above-described immunological reactivity which results from the mixing of several immunological reagents. Further, the broad specificity of the immunoassay of the instant invention is superior to that of the assays contained in certain kits which are currently on the market, and which assay for barbiturates in biological samples. Thus, the immunoassay of the present invention provides a more rapid and accurate barbiturates assay method than methods described in the art or otherwise disclosed to the public because it: (1) requires no specimen treatment before analysis; (2) has a broad-spectrum barbiturate specificity; (3) accurately determines the presence of one or more barbiturates in a sample because antibody specificity precludes the detection of virtually all compounds other than barbiturate-like compounds; (4) precludes the further analysis of samples with unverifiable barbiturate concentrations due to large concentration overestimations because of poor cross-reactivity among the commonly-used barbiturates; and (5) is a homogeneous assay and, thus, unlike heterogeneous immunoassay procedures, the bound tracer need not be separated from the unbound tracer before the end polarization readings are taken.

The immunoassay of the present invention is, thus, particularly advantageous in that it may be used to detect a broad range of barbiturate drugs in bodily fluids without having the problems described in the art (lower sensitivity, poor cross reactivity, and a broad variability from lot to lot of antiserum blend). Such an immunoassay is desirable for use as a screening assay because, in a barbiturate screening assay, it is desirable to have the antibody employed therein react with every barbiturate-like compound in an equivalent manner, and because it has a broad applicability in forensic medicine, in clinical medicine and in industrial settings.

The Reagents and Reagent Kit

Both the immunogens and the tracers of the present invention can be represented by the general structural formula set forth in the Summary of the Invention.

An objective of the novel method of the present invention for determining the presence or amount of barbiturate in a sample is to have competition between barbiturate and the tracer for the recognition sites of the antibody. Great variations in the structure of the haptens and tracers are allowed in achieving this goal. For the purpose of this invention, "haptens" are precursors of the immunogens, comprising generally a substituted barbiturate derivative bearing a group suitable for linking to an immunologically active carrier.

The novel reagent kit of the present invention for determining the presence or amount of barbiturates in biological fluids comprises a salt of a first tracer of the formula shown in FIG. 27 wherein W, $R^1$, $R^3$ Fl and $R^4$ are as defined in the Summary of Invention and antibodies, monoclonal or polyclonal, which have been raised against an immunogen having the structure shown in FIG. 2 wherein W, $R^1$, $R^2$, Q and R are also as defined in the Summary of Invention. Generally, the antibodies will be raised against an immunogen which has a structure similar to a commonly-used barbiturate and the tracer will have a structure which is similar to a commonly-used barbiturate, but which has a structure which is dissimilar to the structure of the immunogen. Preferably, the reagent kit will also contain an amount of riboflavin binding protein which is effective to reduce fluorescence interference by riboflavin. While the most preferred tracer for use in the reagent kit is the tracer shown in FIG. 30, the most preferred antibodies for use in the kit are those generated against the immunogen shown in FIG. 29. The most preferred combination of tracer and antisera for use in the kit are the combination of the tracer shown in FIG. 30 with monoclonal or polyclonal antibodies generated against the immunogen shown in FIG. 29.

The Structure of the Immunogens

Useable antibodies can be produced from a variety of barbiturate derivatives. Immunogens made from compounds functionalized at the 5 position on the ring can produce antibodies in animals; such antibodies are useful in a barbiturates assay according to the invention when combined with the appropriate tracer.

The immunogens of the present invention have the general structural formula shown in FIG. 2, and in the preferred form of the invention, the immunogens are also derived from the general structural formula shown in FIG. 2. The most preferred immunogen of the present invention is shown in FIG. 29. The immunogens can be prepared by coupling a compound of the class shown in FIG. 2 with a poly(amino acid) or a derivative of a poly(amino acid) or another immunologically active carrier, as will be discussed in the context of the synthetic method and the Examples below.

Although thyroglobulin is the poly(amino acid) employed in the most preferred form of the immunogen of the present invention, it should be understood that various protein carriers can be employed, including albumins, serum proteins, e.g., globulins, ocular lens proteins, lipoproteins and the like. Illustrative protein carriers include, in addition to thyroglobulin, thyroxine binding globulin, bovine serum albumin, keyhole limpet hemocyanin, egg ovalbumin, bovine gamma-globulin, etc. Alternatively, synthetic poly (amino acids) having a sufficient number of available carboxylate groups such as aspartates can be employed, as can many other synthetic or natural polymeric materials bearing reactive functional groups. In addition, carbohydrates, yeasts, polysaccharides or any other substance that can be used as an immunological carrier can be conjugated to the hapten to produce an immunogen.

Most of the immunogens of the present invention include a —$CH_2$—, —CH= or a

Figure 21:
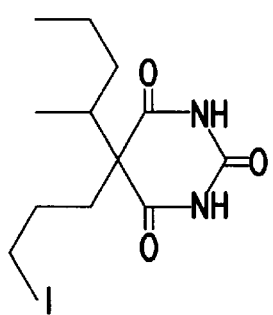
Figure 22:
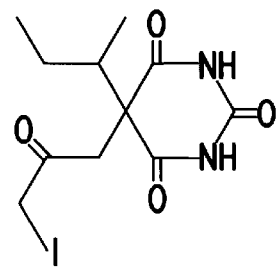
Figure 23:
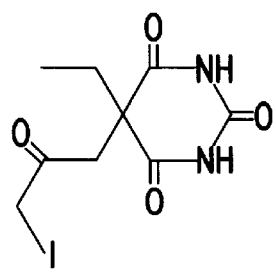
Figure 24:
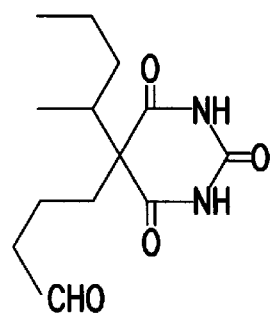
Figure 25:
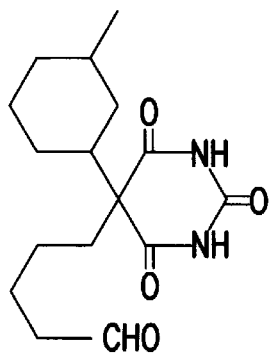
Figure 26:
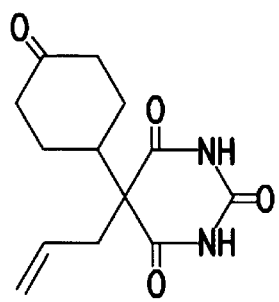

group which links the hapten to the immunogenically active carrier, such that the linkage which directly binds the R variable to the Q variable in the chemical formula shown in FIG. 2 is one other than a peptide linkage. One advantage of these immunogens which has not been disclosed in the art is that the nonpeptide bonds which directly link the hapten component of the immunogens to the immunogenically-active-carrier component of the immunogens of the present invention are extremely stable. Thus, the immunogens are considerably more stable than the immunogens disclosed in the art, such as in Yamaoka et al., J. Immunological Methods 28:51 (1979). Unlike the peptide bonds described by Yamaoka et al., the linkages employed in many of the novel immunogens of the present invention are significantly less susceptible to hydrolysis in a biological environment. For example, FIGS. 21, 22 and 23 of the drawings illustrate novel functionalized haptens which contain an iodoacetamide chemical group, and which can be coupled to an immunogenically active carrier at a basic pH so that a nonpeptide bond is formed. FIGS. 24, 25 and 26 each illustrate haptens which can be coupled to an immunogenically active carrier by the process of reductive amination with the result that a nonpeptide bond is formed.

A preferred immunogen of the present invention has the structure shown in FIG. 28. The most preferred immunogen of the present invention is shown in FIG. 29.

The Structure of the Tracers

The possible variations in the structure of the tracers of the invention are even greater than the possible variations in the structure of the haptens thereof. The tracers of the present invention have the general structural formula shown in FIG. 27 wherein W, $R^1$, $R^3$, Fl and $R^4$ are defined as described in the Summary of the Invention. In a preferred form of the invention, the tracer has the structural formula shown in either FIG. 5 or FIG. 31. The most preferred tracer of the present invention is shown in FIG. 30.

The tracer is a barbiturate derivative that is linked to a fluorescein derivative by, for example, an amino, amidino, triazinylamino, carbamido, thiocarbamido, carbamoyl, thiocarbamoyl, or sulfonylcarbamoyl group, as shown in FIG. 4. The tracers are prepared by linking the appropriate fluorescein derivative to a barbiturate derivative containing an amino, carboxylic acid, sulfonic acid, mercapto, hydroxy, imidate, hydrazide, isocyanate, thioisocyanate, chloroformate, chlorothioformate, carboxylic chloride, chlorosulfonylcarbamoyl, or the like group, as will be discussed in the context of the synthetic method and the Examples below.

By way of example, any of the following fluorescein derivatives can be used:

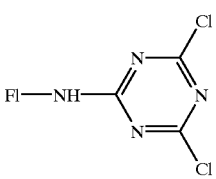

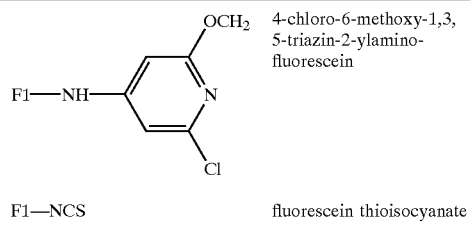

4-chloro-6-methoxy-1,3,5-triazin-2-ylamino-fluorescein

Fl—NCS    fluorescein thioisocyanate

It was unexpectedly discovered that the presence of a carbon-carbon double bond between the fluorescein moiety and the barbiturate ring portions of the novel tracers of the present invention advantageously orients the tracer for optimal interaction with the antibody. Thus, the tracers of the instant invention have an ethylene (—CH═CH—) linkage group between the fluorescein and the ligand component of the tracer and, thus, possesses two unexpected and advantageous qualities: (1) a greater stability; and (2) a decreased interaction between the fluorescein (or fluorescein derivative) and the ligand component of the tracer and, consequently, an enhanced ability to bind to antibodies.

The first quality, that the tracers are surprisingly highly stable due apparently to the double bond in the linking group, is evidenced by the data which is presented in Table 1.

TABLE 1

| Barbiturate Tracer | Temperature (° C.) | Day No. | Polarization (Buffer) | Polarization (Boric Acid) |
|---|---|---|---|---|
| (No Ethylene Linkage) |  | 0 | 247.79 | 269.39 |
|  | 2–8 | 1 | 238.09 | 271.12 |
|  | 2–8 | 7 | 168.21 | 228.62 |
|  | 45 | 1 | 48.70 | 62.68 |
|  | 45 | 7 | >48.70 | >68.68 |
| (Ethylene Linkage) |  | 0 |  | 239.63 |
|  | 2–8 | 1 |  | 235.18 |
|  | 2–8 | 7 |  | 235.08 |
|  | 45 | 1 |  | 237.93 |
|  | 45 | 7 |  | 239.72 |

The data presented above indicate that a tracer which has an ethylene (—CH=CH—) linkage group between the fluorescein and the ligand component of the tracer (lower half of the table) possesses a significantly greater stability at varied temperatures than a tracer which lacks such an ethylene linkage group (upper half of table). While the stability of the tracer which contains an ethylene linkage group is approximately equivalent on days 1 and 7 at both temperatures of 2–8° C. and 45° C., the tracer which lacks such a linkage group is thirty per cent less stable on day 7 at a temperature of 2–8° C. and essentially all-binding capacity is lost (over 80% of the polarization) by day 7 at a temperature of 45° C.

While compounds which lack a double bond have a lifetime of approximately twelve hours, so that they are unstable twelve hours after they have been synthesized, those compounds which contain a double bond remain stable for a significantly longer period of time. The data presented in Tables 2(a) and 2(b) below indicate that a tracer which has an ethylene (—CH=CH—) linkage group between the fluorescein and the ligand component of the tracer remains stable at varied temperatures for a period of at least one and one half years. While a tracer having the chemical structure shown in FIG. 5 was employed to generate the data presented in Table 2(a), a tracer having the chemical structure shown in FIG. 30 was employed to generate the data presented in Table 2(b). These data indicate that the tracer is stable over this long period of time.

TABLE 2(a)

| Time | Temperature (° C.) | Polarization | Average Net Intensity |
|---|---|---|---|
| Day 0 | 2–8 | 209.17 | 3400–5000 |
| Day 1 | 2–8 | 206.61 | 3290–4733 |
| Day 2 | 2–8 | 207.07 | 3200–4670 |
| Day 3 | −20 | 207.38 | 3395–4965 |
|  | 2–8 | 208.05 | 3367–4895 |
|  | 37 | 207.60 | 3400–4910 |
|  | 45 | 205.51 | 3400–4950 |
| Week 1 | −20 | 208.46 | 3300–4800 |
|  | 2–8 | 208.25 | 3400–4900 |
|  | 37 | 202.78 | 3500–5000 |
|  | 45 | 200.11 | 3550–5200 |
| Week 2 | −20 | 208.85 | 3180–4635 |
|  | 2–8 | 210.41 | 3100–4590 |
| Week 4 | 2–8 | 210.35 | 3395–4988 |
| Month 2 | 2–8 | 207.21 | 3282–4777 |
| Month 4 | 2–8 | 205.59 | 3210–4775 |
| Month 8 | 2–8 | 206.85 | 3150–4677 |
| 1 Year | 2–8 | 204.85 | 3161–4615 |
| 18 Months | 2–8 | 199.29 | 3304–4798 |

TABLE 2(b)

| Time | Temperature (° C.) | Polarization | Average Net Intensity |
|---|---|---|---|
| Day 0 | 2–8 | 177.29 | 2686 |
| Day 1 | 2–8 | 177.23 | 2732 |
| Day 2 | 2–8 | 178.32 | 2698 |
| Day 3 | −20 | 178.48 | 2706 |
|  | 2–8 | 176.45 | 2664 |
| Day 4 | 37 | 176.53 | 2649 |
|  | 45 | 176.56 | 2690 |
| Week 1 | 2–8 | 178.69 | 2705 |
|  | 37 | 180.02 | 2710 |
|  | 45 | 175.96 | 2681 |
| Week 2 | 2–8 | 178.01 | 2642 |
|  | 37 | 179.81 | 2652 |
|  | 45 | 172.69 | 2760 |

TABLE 2(b)-continued

| Time | Temperature (° C.) | Polarization | Average Net Intensity |
|---|---|---|---|
| Week 4 | 2–8 | 184.16 | 2669 |
| Month 2½ | 2–8 | 176.47 | 2692 |
| Month 4 | 2–8 | 175.53 | 2665 |
| Month 6½ | 2–8 | 176.90 | 2741 |
| Month 9 | 2–8 | 174.34 | 2816 |

There is a second significant advantage with respect to those compounds which contain a double bond compared to those which lack such a double bond. With respect to compounds which do not contain a double bond, a significant amount of interaction occurs between the fluorescein (or fluorescein derivative) and the ligand component of the compound, with the unfavorable result that the ability of the ligand component to bind to the antibody in an immunoassay is impaired. In contrast, those compounds which contain a double bond possess a resulting rigid stereochemistry. Thus, there is little interaction between the fluorescein (or fluorescein derivative) and the ligand component, such that the ligand component remains free to bind to the antibody in an immunoassay.

The Antibodies

The antibodies of the present invention are prepared by eliciting a response in sheep to the immunogens described supra. The immunogen is administered to animals or to in vitro cultures of immunocompetent cells by a series of innoculations, in a manner well known to those skilled in the art. It should be understood that although sheep were the preferred immune host to barbiturate immunogens in the experiments detailed herein, any in vivo or in vitro host capable of producing antibodies to the structures herein outlined may be employed.

The most preferred antibodies of the present invention are those raised against the immunogen shown in FIG. 29.

The Synthesis of Immunogens

The immunogens of the present invention are made by coupling a hapten, such as shown by the general structure of FIG. 2 when X is chloroformate, aldehyde, carboxylic, amino, chloride, bromide, iodide or hydroxy, to a poly (amino acid) or other immunologically active carrier. The poly(amino acid) or other carrier moiety can be linked to the hapten by a carbamate, amido, thioether, ether, diazo, or amino linkage. In the most preferred embodiment, the poly(amino acid) is thyroglobulin, and the immunogen has the structure shown in FIG. 29.

The immunogens are prepared by coupling a hapten that contains an aldehyde, carboxylic, amino, chlorine, bromine, iodine, hydroxide, or iodoacetonyl group to a poly(amino acid) or other immunologically active carrier. The aldehyde can be coupled by forming a Schiff's base with the poly (amino acid) or the amino group of another immunologically active carrier. A Schiff's base is instantly reduced by sodium cyanoborohydride to form the stable aminomethyl linkage. The activation of the carboxylic groups on the poly(amino acid) can be accomplished by mixing the hapten and the poly(amino acid) with 1-ethyl-3-(3-dimethylamino-propyl) carbo-diimide (EDC), N,N'-dicyclohexylcarbodiimide (DDC), 1-cyclohexyl-3-(2-morpholinoethyl)carbodiimide; methyl-p-toluene sulfonate, or the like. The hydrazide case is coupled in the same manner as for the nonaromatic amino case. Alkyl, chloro, bromo, and iodo derivatives and sulfonate esters alkylate the phenolic hydroxyl groups of tyrosine residues in the carrier protein under strongly alkaline conditions to form alkyl aryl ethers, and alkylate the sulfur of free sulfhydryl groups cysteine to form thioethers. For these reactions the preferred derivatives are the iodoacetonyls and iodides.

The syntheses of the above haptens (immunogen precursors) are accomplished in one of two general ways. FIG. 2 shows an immunogen precursor class in accordance with a preferred embodiment of the method of the present invention. The preparation proceeds from alkylating an appropriate substituted malonate or cyanoacetate ester with a bromoalkylalcohol having a protected alcohol functionality, preferably tetrahydropyranyl ether. The cyclization of such intermediate with urea can be accomplished by treating the mixture of the reactants in solution with a base such as magnesium methoxide, magnesium ethoxide, sodium methoxide, sodium ethoxide, or potassium t-butoxide. The protected functionality is revealed and the compound is coupled to the poly(amino acid) or other carrier.

5-iodoacetonyl barbiturate precursors of immunogens are prepared from appropriate 5,5-disubstituted barbiturates (as shown in FIG. 2), bearing a 5-alkene group with a terminal double bond, by reacting with iodide in water. The 3-hydroxy-iodobarbiturates are prepared in this way. The corresponding α-iodoacetonyl barbiturates are obtained from these by oxidation with chromium-based oxidants such as Jones' reagent or the like.

Aldehydes can be prepared from appropriate 5-alkenyl barbiturates (FIG. 2) bearing a terminal double bond by ozonolysis in methanol at −78° C. Another preferred way to obtain aldehydes (FIG. 2) is by reacting an appropriate substituted malonate ester or cyanoacetate ester with a bromoalkyl aldehyde having protected aldehyde functionality, preferably as acetals. The cyclization of such an intermediate with urea can be accomplished by treating the mixture of the reactants in solution with a base such as sodium ethoxide, sodium methoxide, potassium methoxide, or potassium t-butoxide. The protected functionality is revealed and the compound is coupled to the poly(amino acid) or other carrier.

Carboxylic acids are obtained by the oxidation of appropriate aldehydes with chromium-based oxidants such as Jones' reagent or the like.

A preferred way to synthesize carboxyalkyl barbiturates or carboxyalkenbarbiturates is by reacting appropriate 5-substituted barbiturates (FIG. 2) with halogen alkyl esters or halogen alkenyl esters in the presence of bases such as triethylamine, sodium hydride, potassium t-butoxide, and followed by hydrolysis of appropriate barbiturate esters with a mineral acid such as concentrated hydrochloric acid, 40% sulfuric acid, or the like.

The alkyl halides may be prepared by treatment of the alcohols with hydrogen chloride, hydrogen bromide or hydrogen iodide, or by treatment with halogenating reagents such as thionyl chloride. These halides couple directly to free sulfhydryl groups or carriers under relatively neutral conditions or to phenols such as those-of tyrosyl residues in a poly(amino acid) under strongly basic conditions.

The Synthesis of the Tracers

The structure of two preferred tracers of the present invention are shown in FIGS. 5 and 31. The structure of the most preferred tracer of the present invention is shown in FIG. 30.

The tracers of the present invention are made by coupling a fluorescein moiety, or a derivative of fluorescein, to the general structure shown in FIG. 27, wherein W, $R^1$, $R^3$, Fl and $R^4$ are as defined in the Summary of Invention.

The fluorescein moiety can be linked to the amino, carboxyl, aldehyde, acid chloride, imidate or alkoxy functional group by an amide, amine, urea, thiourea, carbamate, thiocarbamate, triazinylamino or sulfonylcarbamate linkage, as shown in FIG. 4. In the presently preferred embodiment, the fluorescein derivative is aminomethylfluorescein, and this is coupled to a precursor shown in FIG. 27, wherein $R^1$ is (methyl)butyl or 1-methyl propyl and $R_3$ is —$CH_2$, —COOH or —$CH_2$—CH=CH—$CO_2H$. The appropriate carboxyalkenyl barbiturate is coupled to aminoethylfluorescein by first forming a mixed anhydride with the carboxylic acid of the barbiturate. The mixed anhydride is prepared with isobutylchloroformate. The preferred method uses dimethoxyethane.

Other activating groups, such as acid chloride, 1-hydroxybenzotriazole, N-hydroxysuccinimide, p-nitrophenol, and 2-ethyl-5-phenylisoxazolium-3'-sulfonate can be used; and other solvents such as tetrahydrofuran, N,N-dimethyl formamide, dimethysulfoxide, and hexamethylenephosphoramide can be used. The reactants are preferably coupled under conditions for forming amide linkages, and it is most preferred that mixed anhydride procedures be used. Usable tracers can be prepared from a variety of barbiturates.

All barbiturates that have a terminal amino group, such as amino, hydrazinyl, hydrazido, or the like, are coupled to carboxyfluorescein by the active ester method or the mixed anhydride method, and are coupled to fluorescein isothiocyanate, DTAF, or alkoxy DTAF simply by mixing the two materials in solution. The amino group can be converted to isocyanate or thioisocyanate groups by reaction with phosgene and thiophosgene respectively. These are then condensed with aminomethylfluorescein to produce the tracer.

All barbiturates that have a terminal aldehyde group are coupled to aminomethylfluorescein by reductive amination with sodium borohydride.

All barbiturates that have a terminal hydroxy group can be coupled to fluorescein by reaction with phosgene followed by aminomethylfluorescein, DTAF, a-iodoacetamidofluorescein, a-bromoacetamido-fluorescein, or fluorescein isothiocyanate in solution. All barbiturates that have a 5-iodoacetonyl group are coupled to aminomethylfluorescein to produce the tracer.

It should be noted that an aspect of the present invention encompasses the discovery that the presence of a carbon-carbon double bond between the fluorescein moiety and the barbiturate ring advantageously orients the tracer for optimal interaction with the antibody.

The Assay

The particular tracers and antibodies of the present invention have been found to produce surprisingly good results in fluorescence polarization assays for barbiturates.

FIG. 1 shows the general structure of some of the barbiturates to be quantitatively or qualitatively determined in accordance with the present invention.

The assay of the present invention provides a more rapid and accurate barbiturates assay method than most prior art methods because it requires no specimen treatment before analysis and because of the broad-spectrum barbiturate specificity shown by the assay. The assay system accurately determines the presence of barbiturates in a sample, because antibody specificity precludes detection of most compounds other than barbiturate-like compounds.

The novel process of the present invention for determining the presence or amount of barbiturates in biological fluids comprising the steps of:

(a) contacting a sample with a barbiturate antiserum, the barbiturate antiserum containing monoclonal or polyclonal antibodies which have been raised against an immunogen having the structure shown in FIG. 2, wherein W, $R^1$, $R^2$, Q and R are as defined in the Summary of Invention, and with tracer compounds having the structure shown in FIG. 27, wherein W, $R^1$, $R^3$, Fl and $R^4$ are also as defined in the Summary of the Invention, with the tracer compound being capable of producing a detectable fluorescence polarization response to the presence of the barbiturate antiserum;

(b) passing plane polarized light through the resulting solution from step (a) to obtain a fluorescence polarization response; and (c) detecting the fluorescence polarization response of the solution of step (b) as a measure of the presence or amount of barbiturate in the sample.

The most preferred form of this process employs monoclonal or polyclonal antibodies prepared against an immunogen having the structure shown in FIG. 29 with a tracer having the structure shown in FIG. 30. However, another preferred tracer for use with these antibodies is a tracer having the structure shown in FIG. 31.

In accordance with the analytical methods of the present invention, i.e., the methods for determining barbiturates by a fluorescence immunoassay procedure using the tracer compounds and immunogens of the invention, a sample containing or suspected of containing barbiturates is intermixed with a biologically acceptable salt of a tracer and an antibody specific to barbiturates. The antibody is produced using the immunogen as described above. The barbiturates and the tracer compete for limited antibody binding sites, resulting in the formation of complexes. By maintaining constant the concentration of tracer and antibody, the ratio of barbiturates-antibody complex to tracer-antibody complex that is formed is directly proportional to the amount of barbiturates in the sample. Therefore, upon exciting the mixture with plane polarized light and measuring the polarization of the fluorescence emitted by a tracer and a tracer-antibody complex, one is able to determine the presence of barbiturates in the sample.

The results can be quantified in terms of net millipolarization units and span (in millipolarization units). The measurement of net millipolarization units indicates the maximum polarization when a maximum amount of the tracer is bound to the antibody, in the absence of any barbiturate. The higher the net millipolarization units, the better the binding of the tracer to the antibody. The span is the difference between the net millipolarization when tracer is maximally bound to the antibody in the absence of barbiturates and the net millipolarization when tracer is bound to antibody in the presence of specified concentration of barbiturate. The maximum span defines the range of ligand concentration which the assay is able to detect. A larger span provides for a better numerical analysis of data. The preferred antibody-tracer combination has a span of at least 80 millipolarization units. Smaller spans may be acceptable depending on the circumstances.

The pH at which the method of the present invention is practiced must be sufficient to allow the fluorescein moiety of the tracers to exist in their open form. The pH may range from about 3 to 12, more usually in the range of from about 5 to 10, most preferably from about 6 to 9. Various buffers may be used to achieve and maintain the pH during the assay procedure. Representative buffers include borate, phosphate, carbonate, tris, barbital and the like. The particular buffer employed is not critical to the present invention, but the tris and phosphate buffers are preferred. The cation portion of the buffer will generally determine the cation portion of the tracer salt in solution.

Riboflavin binding protein (RBP) may be added to the sample or to one or more of the assay reagents in order to bind any riboflavin present in the sample into RBP-riboflavin complexes, thus eliminating potential fluorescence interference from riboflavin. RBP is a protein of approximately 32,000 M.W. which is commonly isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not critical, provided a sufficient quantity is used to bind virtually all free riboflavin in the sample.

The preferred method of the improved assay of the present invention will now be discussed in detail. The assay is a "homogeneous assay," which means that the end polarization readings are taken from a solution in which bound tracer is not separated from unbound tracer. This is a distinct advantage over heterogeneous immunoassay procedures, such as those where the bound tracer must be separated from the unbound tracer before a reading can be taken.

The reagents for the fluorescence polarization assay of the present invention comprise antibody for barbiturates and barbiturate tracer. Additionally, largely conventional solutions including a pretreatment solution, a dilution buffer, barbiturate calibrators and barbiturates controls are desirably prepared. Typical solutions of these reagents, some of which are described below, are commercially available in assay "kits" from Abbott Laboratories, Abbott Park, Ill.

For the most preferred assay of the present invention, all percentages expressed herein are weight/volume unless otherwise indicated. The tracer formulation presently preferred is 150 nanomolar tracer in: 0.1 molar phosphate buffer at pH 6.2; 5% sodium 5-sulfosalicylate; 0.1% sodium azide; and 0.01% bovine gamma-globulin. The antiserum formulation comprises sheep serum diluted with: 0.1 molar tris buffer at pH 7.5; 0.1% sodium azide; 0.1% bovine gamma-globulin; and 2% ethylene glycol (volume/volume). The dilution buffer comprises: 0.1 molar sodium phosphate at pH 7.5; 0.1% sodium azide; and 0.01% bovine gamma-globulin. The pretreatment solution comprises: 0.01% bovine gamma-globulin; 0.1 molar tris buffer at pH 7.5; 0.1% sodium azide; and 10 mg/mL riboflavin binding protein. Barbiturate calibrators comprising secobarbital in normal human urine at concentrations of 0.0, 200, 400, 700, 1200, and 2000 nanograms per milliliter, with 0.1% sodium azide as a preservative, are useful. Barbiturate controls comprising secobarbital in normal human urine are provided at concentrations of 300, 800 and 1500 nanograms per milliliter with 0.1% sodium azide as a preservative are also useful.

The preferred procedure is especially designed to be used in conjunction with the Abbott $TD_x$® Clinical Analyzer and the Abbott $AD_x$® Drugs of Abuse System, both of which are available from Abbott Laboratories, Abbott Park, Ill. A minimum of fifty microliters of urine is required. The calibrators, controls, or unknown samples are pipetted directly into the sample well of the $TD_x$® or $AD_x$® sample cartridge. One of the advantages of this procedure is that the sample does not require any special preparation. The assay procedure from this point is fully automated.

If a manual assay is being performed, then the sample is mixed with the pretreatment solution in dilution buffer and a background reading is taken. The tracer and antibody are then mixed into the test solution. After incubation, a fluorescence polarization reading is taken.

The net fluorescence polarization value of each calibrator, control or sample is determined and is printed on the output tape of an instrument such as the Abbott TD$_x$® Analyzer. A standard curve has previously been generated in the instrument by plotting the polarization of each calibrator versus its concentration using a nonlinear regression analysis. The concentration of each control or sample is read off the stored calibration curve and printed on the output tape.

With respect to the foregoing preferred procedure, it should be noted that the tracer, antibody, pretreatment solution, calibrators and controls should be stored between about 2° C. and about 8° C. while the dilution buffer should be stored at ambient temperature. A standard curve and controls should be run every two weeks, with each calibrator and control run in duplicate. All samples can be run in duplicate.

It should be understood that the foregoing Detailed Description of the Invention and the following Examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples 1 through 3 describe experiments which were performed in accordance with the concepts of the present invention. Examples 1 through 3 and 25 are directed to the preparation of immunogens useful for producing antibodies; Examples 4 through 8 are directed to the synthesis of precursors for immunogens and tracers; and Examples 9 through 24 and 26 are directed to the preparation of tracers. Example 24 describes the preparation of the most preferred tracer of the present invention and Example 25 describes the preparation of the most preferred immunogen of the present invention.

Example 1

5-(1-methylbutyl)-5-(β-hydroxy-v-iodopropyl) Barbituric Acid 5 g (0.022 mol) of 5-(1-methylbutyl)-5-(allyl)-barbituric acid in 180 mL of water was heated under a reflux condenser to 75–85° C. 6 g of iodide was added to the reaction mixture in small portions over a period of 2 hours. The reaction mixture was stirred and heated for 7 hours. The reaction mixture was cooled down and precipitated. Crystals were filtered off on a Buchner funnel and washed with water. The product was crystallized from ethanol (50 mL) to yield 5.57 g of the desired material.

5-(1-methylbutyl)-5-iodoacetonyl Barbituric Acid 1 g of 5-(1-methylbutyl)-5-(β-hydroxy-v-iodopropyl) barbituric acid was dissolved in 75 mL of acetone. 30 mL of a 0.33 mol solution of potassium dichromate in 10% sulfuric acid was added. The reaction mixture was stirred for 2 hours at room temperature and subsequently extracted with 200 mL of ethyl acetate, washed with brine, water and the organic layer was dried over magnesium sulfate. Ethyl acetate was removed in vacuo and crude solid material crystallized from 70% ethanol. The yield was 519 mg of colorless crystals of the desired product.

Coupling of 5-(1-methyl)iodoacetonyl Barbituric Acid to Bovine Serum Albumin 226 mg of BSA was dissolved in 4.7 mL of phosphate (buffer 0.1 M, pH 8) and 520 ul of N,N'-dimethylformamide. To this solution was added 152 mg of 5-(1-methylbutyl)-5-iodoacetonyl barbituric acid in 530 uL of DMF. The reaction mixture was stirred at room temperature for 36 hours. The resulting solution was dialyzed exhaustively versus water and liophilized to give 208 mg of the desired conjugate.

Example 2

1-Bromoethyl Tetrahydropyranylether

To 2-bromoethanol (125 g, 1.0 equiv), cooled in an ice bath, was added p-toluenesulfonic acid monohydrate (catalytic amount). Dihydropyran (93 g, 1.1 equiv) was added dropwise, with stirring, under an argon atmosphere. When the addition was complete, the reaction was stirred for 1 hour at room temperature. The residue was purified by short path distillation, giving approximately 125 g of product.

Phenyl-tetrahydropyranyloxyethyl Diethyl Malonate

To diethyl phenylmalonate (76 mL, 1.0 equiv) in DMF was added NaH (13.1 g, 1.0 equiv, 64.14% mineral oil dispersion). The reaction was stirred for ½ hour at 50° C. then 1-bromo-2-tetrahydropyranylethanol (80 mL, 1.5 equiv) was added and the reaction stirred at 60° C. for 18 hours. The reaction mixture was neutralized and the solvent removed under reduced pressure. The residue was purified by short path distillation, giving about 46 g of product.

THP-hydroxyethylphenobarbital

Magnesium turnings (3.7 g, 1.2 equiv) were dissolved in dry methanol under an argon atmosphere. The THP-malonate (46 g, 1.0 equiv) and urea (9.9 g, 1.3 equiv) were dissolved together in dry methanol and then added to the magnesium solution. After refluxing for 48 hours, additional urea (9.9 g, 1.3 equiv) and magnesium methoxide (3.7 g of Mg, 1.2 equiv) were added. After refluxing an additional 24 hours, the solvent was removed under reduced pressure and the residue taken up in 5% aqueous HCl, then extracted with ether. The product was removed from the ether layer and crystallized from ether/hexane, giving about 13 g of material.

5-Phenyl-5-hydroxyethyl Barbituric Acid

THP-hydroxyethylphenobarbital (19 g) was dissolved in acetic acid:water (50/50) with heat. The solution was refluxed and the deprotection monitored by TLC (silica gel, 10:90, methanol:methylene chloride). When the reaction was complete, the solvent was removed under reduced pressure and the residue crystallized from ethanol:water. The yield was 8.7 grams of the product as a white powder.

Conjugation of 5-Phenyl-5-hydroxyethyl Barbituric Acid to BSA

Hydroxyethylphenylbarbital (500 mg) was suspended in dry, freshly distilled THF (10 mL). Phosgene was bubbled into the solution with stirring for 15 minutes, following which argon was bubbled into the solution to remove the excess phosgene. After 15 minutes, the THF was removed under reduced pressure and the residue triturated with ethyl ether. After drying, the yield was about 520 mg of the product as a white powder.

To a solution of BSA (500 mg, 1.0 equiv) in 0.1 N, (pH 8) phosphate buffer (7 mL) was added first DMF (3 mL) and then the chloroformate of hydroxyethyl phenobarbital (50 mg) which had been dissolved in THF (1 mL) was added to the resulting solution. The chloroformate was added with vigorous stirring, and the reaction was stirred for an additional 3 hours.

The solution was purified using a PID column, eluting with distilled water. Two peaks were collected, the first containing 100 mg of product and the second containing 400 mg of product. Examination by ultraviolet light indicated that both samples contained protein and phenobarbital.

Example 3

Diethyl-2-(1-methylbutyl)malonate

Sodium metal (5.24 g, 0.23 g atm) was reacted with 25 mL of absolute ethanol. To this solution was added dropwise, with stirring, diethyl malonate (36.0 mL, 0.24 mol). The solution was heated to reflux and 2-bromopentane (29.0 mL, 0.23 mol) was added dropwise. After refluxing overnight, the reaction was cooled and the ethanol removed on a rotovap. The product was washed with water, dried with $MgSO_4$ and fractionally distilled to give 35.7 g of the desired product.

Diethyl-2-(1-methylbutyl)-2-(5-pentenyl)-malonate

Potassium metal (1.71 g., 0.04 g atm) was reacted with 30 mL of anhydrous t-butyl alcohol. The reaction was then heated to 75° C. and diethyl 2-(1-methylbutyl)-malonate (10.03 g, 0.04 mol) was added dropwise. After refluxing for four hours, 1-bromo-5-pentene (6.4 g, 0.04 mol) was added dropwise with stirring. The reaction was refluxed overnight and was then poured into water and extracted with ether. The ether extracts were dried with $MgSo_4$ and the ether evaporated on the rotovap to give the desired material.

5-(1-Methylbutyl)-5-(pentenyl)-barbituric Acid

Sodium metal (0.98 g, 0.04 g atm) was reacted with methanol (15 mL) followed by the addition of urea (5.14 g, 0.09 mol). Diethyl 2-(1-methyl-butyl)-2-(5-pentenyl)-malonate (6.08 g, 0.02 mol) was then added. After refluxing for two days the methanol was distilled off. The residue was dissolved in 1 N sodium hydroxide solution, extracted with ether and then made acidic with hydrochloric acid to give a white precipitate of the barbituric acid.

5-(4-Butanal)-5-(1-methylbutyl)-barbituric Acid

Ozone was passed through a solution of the above barbiturate in methanol at −78° C. After the solution had turned blue, nitrogen was bubbled in to remove excess ozone. Dimethyl sulfide was then added and the solution stirred overnight at room temperature. The solvents were then removed under vacuum to give 0.62 g of the desired aldehyde.

Conjugation of the Above Aldehyde to BSA

To a solution of 25 mL of water, 5 mL of dimethylformamide and 5 mL of ethanol was added 188 mg of BSA. The pH of the solution was adjusted to 6.2 and the above aldehyde added (18.6 mg, 0.07 mmol). After stirring for one hour, sodium cyanoborohydride (472 mg, 7.5 mmol) was added and the reaction stirred overnight. The material was then dialyzed against water with a pH of 9 and then against water with a pH of 7. The material was then freeze dried to give 113 mg of the barbituric acid BSA conjugate.

Example 4

5-(1-Methylbutyl)-5-formylmethyl Barbituric Acid

To a solution of sodium secobarbital (5.30 g, 22.2 mmol) in methanol was passed a stream of ozone until the solution turned a blue color. After excess ozone was removed by passing nitrogen through the reaction dimethyl sulfide (14 mL) was added. The reaction was stirred at room temperature overnight before solvents were removed on a rotovap. The aldehyde was then purified on silica prep plates using ethyl acetate:hexanes (1:1).

Example 5

Dimethyl-2-(3-methylcyclohexyl)-malonate

Sodium metal (7.02 g, 0.30 g atm) was reacted with anhydrous methanol (250 mL). To this was then added dimethyl malonate (70 mL) dropwise while the temperature of the reaction was maintained at 50° C. To this solution was then added dropwise 3-methylcyclohexylbromide (54.0 g, 0.30 mol) and the reaction refluxed overnight. The methanol was removed on a rotovap and the remaining material partitioned between ether and water. The ether layer was separated, dried with $MgSO_4$ and evaporated to give a yellow oil. Distillation of the material at 95–106° C. and 1.2 mm pressure gave a clear oil.

Dimethyl 2-(5-hexenyl)-2-(3-methylcyclohexyl)-malonate

To a slurry of sodium hydride (2.53 g, 0.06 mol) in anhydrous N,N-dimethylformamide (50 mL) was added dropwise dimethyl 2-(3-methylcyclohexyl)-malonate (14.46 g, 0.06 mol). After complete addition, the reaction was stirred until no more hydrogen gas was evolved. To the reaction was then added dropwise 1-bromo-6-hexene (10.33 g, 0.06 mol) followed by stirring. The progress of the reaction was followed by analytical chromatography using silica plates and ethyl acetate:hexanes (40:60). After complete reaction, water (20 mL) was added and most of the solvents removed under high vacuum. The remaining material was partitioned between water and ether and the ether layer washed twice with water. The ether solution was dried with $MgSO_4$ and evaporated to give a thick yellow oil. The product was then distilled at 127–134° C. and 0.4 mm pressure to give clear oil.

5-(3-Methylcyclohexyl)-5-(5-hexenyl)-barbituric Acid

Sodium metal (1.24 g, 0.05 g atm) was reacted with absolute ethanol (75 mL). After the reaction was complete, urea (5.16 g, 0.08 mol) was added followed by the addition of the above malonate (6.67 g, 0.02 mol). After refluxing sixty hours, the ethanol was evaporated and the material partitioned between water (pH 4) and ethyl acetate. The ethyl acetate was dried with $MgSo_4$ and evaporated to give a white gummy material. The material was then purified on silica prep plates using ethyl acetate/hexane (40/60) to give the purified barbituric acid.

5-(3-Methylcyclohexyl)-5-formylbutyl-barbituric Acid

Ozone was passed through a solution of the barbituric acid above (40 mg, 0.13 mmol) dissolved in methanol (20 mL) until the solution turned blue. Nitrogen was passed through the solution to remove excess ozone, and dimethyl sulfide (2 mL) was added. After stirring overnight, the solvents were removed to give the desired aldehyde as a white gummy material.

Example 6

Secbutyl Dimethyl Malonate

Sodium metal (6.9 g) was reacted with 120 mL of anhydrous methanol. To this solution was added 39.6 g (0.3 mol) of dimethylmalonate. The reaction mixture was refluxed, and 2-bromobutane (41.1 g, 0.3 mol) was added. After refluxing for 16 hours, the reaction mixture was cooled and methanol removed in vacuo. The product was extracted with ethyl ether and then washed with water and half saturated brine. Organics were dried over magnesium sulfate. After removal of ethyl ether by evaporation in vacuo, the crude oil was fractionally distilled to give 24 g of desired product (bp 95–105° C./15 mm Hg).

5-Secbutyl Barbituric Acid 110 mL of anhydrous ethanol was reacted with 7.72 g of sodium metal. Subsequently 17.6 g (0.1 mol) of dimethyl secbutylmalonate was added, followed (after about 5 minutes) by urea (6.72 g). The reaction mixture was refluxed for 15 hours and 60 mL of ethanol was distilled off. 200 mL of water was added to the residue followed by 20 mL of concentrated sulfuric acid. Precipitated crystals were filtered off. The product was then recrystallized from water to yield 8 g of colorless crystals.

5-Secbutyl-5-(carbethoxy-1-propylene) Barbituric Acid

In a 2-neck 100 mL flask was placed 265 mg (6.625 mmol) of sodium hydride (60% oil suspension). The sodium hydride was washed with hexanes, and then 1219 mg of 5 secbutylbarbituric acid in 5 mL THF was added, followed by 50 mL of dimethylformamide. The reaction mixture was stirred at room temperature for 1.5 hours, and 912 uL of ethylbromocrotonate was added, followed by 900 mg of anhydrous potassium iodide. The reaction mixture was refluxed for 48 hours and subsequently rotoevaporated to dryness. The residue was extracted with ethyl acetate, washed with water, 5% sodium bisulfite, brine and then, dried over magnesium sulfate. The solvent was removed, and the crude material was purified by column chromatography on silica gel using ethyl acetate as an eluent. The yield was 78% of desired product.

5-Secbutyl-5-(carboxy-1-propylene) Barbituric Acid 152 mg of 5-secbutyl-5-carbethoxy-1-propylene barbituric acid in 15 mL of concentrated hydrochloric acid was refluxed for 45 minutes. The reaction mixture was evaporated to dryness to yield the desired product as colorless crystals. (Yield 95%, mp 168–171° C.)

Example 7

250 mg of 5-(1-methylbutyl)-5-carbethoxymethyl barbituric acid in 25 mL of concentrated hydrochloric acid was refluxed for 45 minutes. The reaction mixture was cooled, and the precipitated crystals were filtered off. Recrystallization from water gave 190 mg of colorless crystals (mp 238–240° C.).

Example 8

200 mg of 5-(1-methylbutyl)-5-carbethoxypropyl barbituric acid was refluxed for 1 hour with 25 mL of concentrated hydrochloric acid. The reaction mixture was evaporated in vacuo and the solid residue was crystallized from water. Yield 120 mg of colorless crystals, mp 189–192° C.

Example 9

Coupling of 5-Secbutyl-5-carboxy-1-propylene Barbituric Acid with Aminomethylfluorescein 26.8 mg (0.1 mmol) of 5-secbutyl-5-carboxy1-propylene barbituric acid was dissolved in 0.3 mL of anhydrous DMF and to this solution was added 20 mg of dicyclohexylcarbodiimide dissolved in 0.3 mL of DMF, followed by 11.5 mg of N-hydroxysuccinimide in 0.3 mL of DMF. The reaction mixture was stirred at room temperature. After 30 minutes, 42 mg of aminomethylfluorescein was added. After 20 hours, the reaction mixture was rotoevaporated to dryness and purified by column chromatography on silica gel using ethyl acetate:acetic acid (100:0.2) as an eluent.

Example 10

Coupling of 5-(1-Methylbutyl)-5-carboxy-1-propylene Barbituric Acid with Aminomethylfluorescein This compound was prepared according to the procedure of Example 9, starting from 28.2 mg (0.1 mmol) of 5-(1-methylbutyl)-5-carboxycrotonoyl barbituric acid, 11.5 mg of N-hydroxysuccinimide, 20 mg of dicyclohexylcarbodiimide, and 42 mg of aminomethylfluorescein. The product was purified by preparative thin layer chromatography on silica gel using ethyl acetate:acetic acid (100:0.2) as an eluent.

Example 11

Coupling of 5-Isopropyl-5-(carboxy-1-propylene) Barbituric Acid with Aminomethylfluorescein This compound was prepared according to the procedure of Example 9, starting with 21.4 mg of 5-ethyl-5-carboxymethyl barbituric acid, 11.5 mg of N-hydroxysuccinimide, 20 mg of dicyclohexylcarbodiimide and 42 mg of aminomethylfluorescein. The product was purified by preparative thin layer chromatography on silica gel using ethyl acetate:acetic acid (100:0.2) as an eluent.

Example 12

Coupling of 5-Ethyl-5-carboxymethyl Barbituric Acid to Aminomethylfluorescein

This compound was prepared according to the procedure of Example 9 starting with 21.4 of 5-ethyl-5-carboxymethyl barbituric acid, 11.5 mg of N-hydroxysuccinimide, 20 mg of dicyclohexylcarbodiimide and 42 mg of aminomethylfluorescein. The product was purified by chromatography on silica gel using ethyl acetate:acetic acid (100:0.2) as an eluent.

Example 13

Coupling of 5-Secbutyl-5-carboxymethyl Barbituric Acid with Aminomethylfluorescein This compound was prepared according to the procedure of Example 9, starting with 24 mg of 5-secbutyl-5-carboxymethyl barbituric acid, 11.5 mg of N-hydroxysuccinimide, 20 mg of dicyclohexylcarbodiimide and 42 mg of aminomethylfluorescein. The product was purified by preparative thin layer chromatography (PTLC) on silica gel using ethyl acetate:acetic acid (100:0.2) as an eluent.

Example 14

Coupling of Secbutyl-5-carboxyethyl Barbituric Acid with Aminomethylfluorescein

This compound was prepared according to the procedure of Example 9, starting with 26 mg of 5-secbutyl-5- carboxyethyl barbituric acid, 11.5 mg of N-hydroxysuccinimide, 20 mg of dicyclohexyl carbodiimide and 42 mg of aminomethylfluorescein. The product was purified by PTLC on silica gel using ethyl acetate:acetic acid (100:0.2) as an eluent.

Example 15

Coupling of 5-Secbutyl-5-carboxypropyl Barbituric Acid with Aminomethylfluorescein This compound was prepared according to the procedure of Example 9, starting with 28 mg of 5-secbutyl-5-carboxypropyl barbituric acid, 11.5 mg of N-hydroxysuccinimide, 20 mg of dicyclohexylcarbodiimide and 42 mg of aminomethylfluorescein. The product was purified by PTLC using ethyl acetate:acetic acid (100:0.2) as an eluent.

Example 16

Coupling of 5-Secbutyl-5-carboxybutyl Barbituric Acid with Aminomethylfluorescein This compound was prepared according to the procedure of Example 9, starting with 29 mg of 5-secbutyl-5-carboxybutyl barbituric acid, 11.5 mg of N-hydroxysuccinimide, 20 mg of dicyclohexylcarbodiimide, and 42 mg of aminomethylfluorescein. The product was purified by PTLC using ethyl acetate:acetic acid, (100:0.2) as an eluent.

Example 17

Coupling of 5-1-(methylbutyl)-5-carboxy Methyl Barbituric Acid with Aminomethylfluorescein This compound was prepared according to the procedure of Example 9 starting with 24 mg of 5-(1-methylbutyl)-5-carboxymethylbarbituric acid, 11.5 mg of N-hydroxysuccinimde, 20 mg of dicyclohexylcarbodiimide and 42 mg of aminomethylfluorescein. The product was purified by PTLC on silica gel using ethyl acetate-acetic acid, 100:0.2 as an eluent.

Example 18

Coupling of 5-(1-methylbutyl)-5-carboxyethyl Barbituric Acid with Aminomethylfluorescein This compound was prepared according to the procedure of Example 9, starting with 25 mg of 5-(1-methylbutyl)-5-carboxyethyl barbituric acid, 11.5 mg of N-hydroxysuccinimide, 20 mg of dicyclohexylcarbodiimide and 42 mg of aminomethylfluorescein. The product was purified by PTLC on silica gel using ethyl acetate:acetic acid, (100:0.2) as an eluent.

Example 19

Coupling of 5-(1-Methylbutyl)-5-carboxypropyl Barbituric Acid with Aminomethylfluorescein This compound was prepared according to the procedure of Example 9, starting with 26.5 mg of 5-(l-methylbutyl)-5-carboxypropyl barbituric acid, 11.5 mg of N-hydroxysuccinimide, 20 mg of dicyclohexylcarbodiimide and 42 mg of aminomethylfluorescein. The product was purified by PTLC on silica gel using ethyl acetate:acetic acid, (100:0.2) as an eluent.

Example 20

Coupling of 5-(1-Methylbutyl)-5-carboxybutyl Barbituric Acid with Aminomethylfluorescein This compound was prepared according to the procedure of Example 9, starting with 28 mg of 5-(1-methylbutyl)-5-carboxybutyl barbituric acid, 11.5 mg of N-hydroxysuccinimide, 20 mg of dicyclohexylcarbodiimide and 42 mg of aminomethylfluorescein. The product was purified by PTLC on silica gel using ethyl acetate:acetic acid (100:0.2) as an eluent.

Example 21

Conjugation of 5-(1-Methylbutyl)-5-carboxymethyl Barbituric Acid to Fluoresceinamide (Isomer)

To the 5-(1-Methylbutyl)-5-carboxymethyl barbituric acid (58.3 mg) was added thionyl chloride (2 mL) and the solution refluxed for 1.5 hours. Excess of thionyl chloride was removed in vacuo and the oil cooled. To this was added a solution of fluoresceinamide (isomer 1) in dry pyridine (1 mL). Chromatography of the material on silica prep plates using ethyl acetate:acetic acid (100:0.2) gave the desired tracer.

Example 22

Conjugation of 5-(3-Methylcyclohexyl)-5-carboxybutyl Barbituric Acid

This compound was prepared according to the procedure of Example 9, starting from 21 mg of 5-(3-methylcyclohexyl)-5-carboxybutyl barbituric acid, 6.9 mg of N-hydroxysuccinimide, 19.9 mg of dicyclohexylcarbodiimide and 24 mg of aminomethylfluorescein.

Example 23

Conjugation of 5-(1-methylbutyl)-5-formyl Methylbarbituric Acid to Aminomethylfluorescein To a solution of 2 mL of water and 2 mL of methanol at pH 6 was added 5-(1-methylbutyl)-5-formyl-methylbarbituric acid (141 mg, 0.58 mmol) and aminomethylfluorescein (210 mg, 0.58 mmol). The solution was completed by the dropwise addition of N,N-dimethylformamide. After stirring for 1 hour, sodium cyanoborohydride (38.8 mg) was added all at once. After stirring overnight, the solvents were evaporated and the material purified on reversed phase preparative plates (silica gel) using methanol/water/trifluoroacetic acid as an eluent.

Example 24

Diethyl Cyclopentylmalonate
(Preparation of the Most Preferred Tracer—FIG. 30)

To a solution of 4.6 g (0.2 mole) of sodium metal in 80 mL of absolute ethanol was added 30.4 mL (0.2 mole) of diethyl malonate. Brief stirring of the resulting mixture caused a thick, white precipitate to appear. To this suspension was added 21.4 mL (0.2 mole) of cyclopentyl bromide. The mixture was heated for 12 hours and then cooled to ambient temperature. Most of the ethanol was removed via rotary evaporation, and the resulting residue was diluted with 250 mL of water and extracted 3×100 mL with diethyl ether. The combined extracts were dried over $MgSO_4$, filtered, and concentrated. Distillation through a 6" Vigreaux column at 6 mm Hg provided 32.232 g of a colorless liquid with a boiling point of 122–125° C.

5-Cyclopentylbarbituric Acid

To a solution of 3.48 g (151 mmol) of sodium in 50 mL absolute ethanol was added 3.02 g (50 mmol) urea and 10 g (44 mmol) of the diethyl cyclopentylmalonate prepared above. The thick white slurry which formed was refluxed for 12 hours. Most of the ethanol was removed via rotary evaporation, and the residue was diluted with 100 mL of water and acidified with 10 mL of 98% $H_2SO_4$. The resulting white solid which formed was collected by filtration and dried on a pump. The solid was recrystallized from water, and recrystallized a second time from 5% water/ethanol to obtain 7.006 g of colorless platelike crystals with a melting point of 222–223° C.

5-Cyclopentyl-5-[ethoxycarbonyl)-2-propenyl] Barbituric Acid

A solution of 200 mg (1.02 mmol) of the barbituric acid prepared in the experiment directly above in a mixture of 1.0 mL tetrahydrofuran and 1.0 mL dimethylformamide was added to a suspension of 32 mg (80% mineral oil dispersion, 1.07 mmol) sodium hydride, previously washed 3×5 mL with pentane, in 1.0 mL dimethylformamide. After stirring for 1 hour at ambient temperature, 168 uL (1.22 mmol) ethyl 4-bromocrotonate was added, the reaction was warmed to 70° C. and stirred for 12 hours. The solution was cooled, concentrated on a rotovap, diluted with ethyl acetate, and washed 2×1 mL with water. The solution was dried over $MgSO_4$ and concentrated. Chromatography on a 1×18 cm column, packed with hexane and eluted with 50 mL each of 10%, 20%, 30%, 50% and 70% ethyl acetate/hexanes, provided 297 mg of a clear pale yellow oil.

5-Cyclopentyl-5-[3-carboxy-2-propenyl]barbituric Acid

To a solution of 292 mg (0.94 mmol) of the ester prepared in the previous experiment in 1.0 mL dimethoxyethane was added 5.0 mL of a 15% $H_2SO_4$ solution in water. The mixture was refluxed for 45 minutes and cooled. The solution was concentrated to a thick oil, diluted with ethyl acetate, and washed 2×1 mL with water. Drying over $MgSO_4$ and solvent removal produced 246 mg of an off-white solid. The solid was boiled in 6 mL water and cooled, to provide 132 mg of a white solid with a melting point of 226–227° C., which crystallized and was isolated by filtration.

5-[3-[(2a-Fluoresceinyl)methylaminocarbonyloxy]-2-propenyl]-5-cyclopentyl-barbituric Acid To a cooled (0° C.) solution of 7.8 mg (27 umol) of the acid prepared in the previous experiment in 300 uL dimethoxyethane was added 3.6 uL (27 umol) of isobutyl chloroformate. The solution was warmed to ambient temperature and stirred for 1.3 hours. The solution was recooled to 0° C., and a second-solution of 10.9 mg (27 umol) aminomethylfluorescein hydrochloride and 7.6 uL (54 umol) triethylamine in 200 uL of dimethylformamide was added, and the solution was warmed to ambient temperature and stirred for 12 hours. The solvents were pumped off, and the residue was purified by preparative thin layer chromatography, with 80% methanol/chloroform as eluent. Elution of the major fluorescent band with 10% methanol/chloroform provided after concentration 10.2 mg of an orange solid.

Example 25

Diethyl Cyclopentenylmalonate
(Preparation of the Most Preferred Immunogen—FIG. 29)

To 174 g (2.63 mol) of freshly depolymerized cyclopentadiene cooled and maintained at −78° C. was added 87.5 g (2.50 mol) gaseous HCl. Meanwhile, 152 mL (1.0 mol) diethyl malonate was added to a solution of 21.4 g (0.93 mol) sodium in 400 mL absolute ethanol. After HCl addition was complete, the crude yellow chloride maintained at −78° C. was added in 1 mL portions to the malonate solution. Considerable heat was produced, the yellow color dissipated, and copious white precipitate formed as each portion was added. The suspension was then stirred for 17 hours, most of the ethanol removed by rotary evaporation, and the reaction quenched with 200 mL water and extracted 5×100 mL with diethyl ether. The combined extracts were dried over $MgSo_4$, filtered, and concentrated to a clear yellow oil. Distillation of a portion of this material at 0.5 mm Hg yielded 19.091 g of a clear green oil, with a boiling point of 91–94° C.

5-(2-Cyclopentenyl)barbituric Acid

This barbituric acid was synthesized according to the procedure described above for 5-cyclopentylbarbituric acid.

5-(2-Cyclopentenyl)-5-[3-(ethoxycarbonyl)propyl] barbituric Acid

To a suspension of 434 mg (3.79 mmol) of potassium hydride, previously washed 3×5 mL with hexane, in a mixture of 4 mL tetrahydrofuran and 17 mL dimethylformamide was added 700 mg (3.60 mmol) of the 5-(2-cyclopentenyl)barbituric acid prepared above. The mixture was stirred for 1 hour, after which 0.51 mL (3.96 mmol) ethyl 2-bromopropionate and 178 mg (1.18 mmol) anhydrous sodium iodide was added. The solution was refluxed for 12 hours, and allowed to cool to ambient temperature and then stirred for 72 hours. Most of the solvents were removed by rotary evaporation, and the reaction was quenched with water, and extracted 4×10 mL with ethyl acetate. The combined extracts were dried over $MgSO_4$, filtered, and concentrated. Chromatography on silica gel, eluting with 5% methanol/chloroform, produced 917 mg of a pale yellow oil.

5-(2-Cyclopentenyl)-5-(3-carboxypropyl)barbituric Acid

To a solution of 737 mg (2.51 mmol) of the ester prepared in the preceding experiment in 2 mL tetrahydrofuran was added 6 mL of a 5% sulfuric acid/water solution. The mixture was stirred at ambient temperature for several days. The reaction was concentrated on a rotovap, and the residue was chromatographed on silica gel, eluting with 2%, 5%, and 10% methanol/chloroform, to provide 215 mg of a white crystalline material.

Coupling of 5-(2-Cyclopentenyl)-5-carboxypropyl Barbituric Acid to Thyroglobulin 5-(2-cyclopentenyl)-5-carboxypropyl barbituric acid was coupled to thyroglobulin as the mixed anhydride by dissolving 12.65 mg (4.7×10 moles) of 5-(2-cyclopentenyl)-5-carboxypropyl barbituric acid in 1.0 mL of p-dioxane. To this mixture was added $8×10^{-5}$ moles of triethylamine and $8×10^{-5}$ moles of isobutylchloroformate. The reaction was stirred at room temperature for 2 hours during which time a fine white precipitate formed. This suspension was added to a rapidly stirring solution of bovine thyroglobulin (200 mg) which was dissolved in 11.0 mL of 0.05 M sodium borate, pH 9.5. After stirring at room temperature for 2 hours, the mixture was dialyzed against 4 changes (2 liters each) of 0.05 M sodium phosphate, pH 7.5. Dialysis was carried out at 2–8° C. and at least 8 hours elapsed between each change of dialysis buffer. After dialysis, the final protein concentration was determined by the Lowry Method (*J. Biol. Chem.*, Vol. 193, Pg. 265–275 (1951)) and the degree of substitution was determined by TNBS (trinitrobenzene sulfonate) titration.

Example 26

Diethyl [3-Methyl-2-butenyl]malonate
(Preparation of a Preferred Tracer—FIG. 31)

To a cooled (0° C.) suspension of 422 mg sodium hydride (80% dispersion in mineral oil, 14.1 mmol, previously washed 3×3 mL with pentane) in a mixture of 10 mL tetrahydrofuran and 5 mL dimethylformamide was added 2.04 mL diethyl malonate (13.4 mmol). The mixture was warmed to ambient temperature and stirred for 0.6 hours. Prenyl bromide (2.00 g, 13.4 mmol) was then injected, and the solution was stirred for 30 minutes at ambient temperature and then for 1 hour at reflux. The solution was then allowed to cool to ambient temperature and stirred for 12 hours. The reaction was quenched with water, acidified with 10% aqueous sulfuric acid to pH 3, and extracted 2×10 mL with ether. The combined washings were dried over anhydrous magnesium sulfate and concentrated. Chromatography on silica gel, eluting with 4%, 7%, and 10% ether/hexane provided 2.734 g clear colorless oil upon concentration.

5-[3-Methyl-2-butenyl]barbituric Acid

To a solution of 70 mg sodium (3.03 mmol) in 1.0 mL absolute ethanol was added 61 mg urea (1.01 mmol), followed by 200 mg of the diethyl prenylmalonate (0.88 mmol) prepared in the previous experiment. The solution was refluxed gently for 12 hours. Most of the ethanol was removed by rotary evaporation, and the residue was diluted in water. The solution was acidified to pH 3 and extracted 2×10 mL with ethyl acetate. The combined organic phases were dried over anhydrous magnesium sulfate and concentrated to 214 mg of an off-white solid.

5-[3-Methyl-2-butenyl]-5-allylbarbituric Acid

The solid prepared in the previous reaction was dissolved in a mixture of 0.5 mL tetrahydrofuran and 1.0 mL dimethylformamide, 33 mg sodium hydride (80% dispersion in mineral oil, 1.09 mmol) was added, and the mixture was stirred for 1 hour. Allyl bromide (0.11 mL, 1.13 mmol) was then added, and the solution was stirred for 72 hours at ambient temperature. The reaction was quenched with dilute hydrochloric acid to pH 3 and extracted 3×10 mL with ethyl acetate. The combined extracts were dried over anhydrous magnesium sulfate and concentrated. Chromatography on silica gel, eluting with 20%, 30%, and 40% ethyl acetate/hexane, provided 100 mg of a colorless oil.

5-[4-Hydroxy-3-methyl-2-butenyl]-5-allylbarbituric Acid

To a solution of the barbituric acid derivative prepared in the preceding experiment (100 mg, 0.42 mmol) in 1.0 mL dichloromethane was added 6 mg (42 umol) salicylic acid and 9 mg (84 umol) selenium dioxide. The suspension was placed in a water bath, and 0.29 mL (3.8M, 1.09 mmol) of a anhydrous solution of tert-butyl hydroperoxide in benzene was added. The suspension was then vigorously stirred for 12 hours at ambient temperature. The reaction mixture was concentrated, and chromatographed directly on a silica gel column, eluting with 40%, 50%, 60%, and 70% ethyl acetate/hexane. In addition to some starting material as well as other products, 21 mg of a colorless oil was isolated.

5-[4-[(2a-Fluoresceinyl)methylaminocarbonyloxy]-3 methyl-2-butenyl]-5-allylbarbituric Acid To a cooled (0° C.) solution of 5 mg (20 umol) of the oil prepared in the previous experiment in 200 uL tetrahydrofuran was added 200 uL of a 12% solution of phosgene in benzene. The solution was warmed to ambient temperature and stirred for 0.6 hours. The solvents were removed by rotary evaporation, and the residue was redissolved in 100 uL dimethylformamide, and a solution of 8 mg (20 umol) aminomethylfluoresceine hydrochloride in a mixture of 200 uL dimethylformamide and 5.6 uL (40 umol) triethylamine was added. The solution was stirred at ambient temperature for 12 hours. The solvents were pumped off, and the residue was purified by thin layer chromatography, eluting with 10% methanol/chloroform. Elution of the major band with 80% methanol/chloroform provided 6.6 mg of an orange solid after concentration.

An antibody for barbiturates which has been raised against an immunogen with the structure shown in FIG. 28 and the barbiturate tracer shown in FIG. 5 have been found to produce surprisingly good results in fluorescence polarization immunoassays for barbiturates. The most preferred combination of tracer and antibody, however, is the combination of a tracer having the structure shown in FIG. 30 with monoclonal or polyclonal antibodies raised against an immunogen having the structure shown in FIG. 29.

An additional advantage of the method of the present invention is that the sensitivity of the assay, which is defined as the lowest measurable concentration of analyte which can be distinguished from zero with 95% confidence, is approximately 60 ng/mL as measured against secobarbital.

Another significant advantage of the method of the present invention is cross-reactivity to a large number of the commonly-used barbiturates. Cross-reactivity was tested by the method of the present invention for the commonly-used barbiturates. In each case, compounds were assayed on the Abbott Laboratories+ $TD_x$® Clinical Analyzer or the $AD_x$® Drugs of Abuse System after adding a known quantity (200 ng/mL) of the barbiturate test compound to drug-free normal human urine.

Representative cross-reactivity data for the commonly-used barbiturates employing the assay of the present invention wherein the tracer has the structure shown in FIG. 5 and the antibodies have been raised against an immunogen having the structure shown in FIG. 28 are shown in Table 3(a) below. The five columns indicate the following information:

(1) Column 1—Indicates the particular barbiturate assayed for;
(2) Column 2—Indicates the amount of the barbiturate test compound added to the drug-free urine;
(3) Column 3—Indicates the amount of the barbiturate test compound found in the resulting human urine;
(4) Column 4—Indicates the factor which either overestimates (a number greater than 1.0, such as 1.33) or underestimates (a number less than 1.0, such as 0.83) the particular barbiturate assayed for; and
(5) Column 5—Indicates the percent cross reactivity.

TABLE 3(a)

| 1 | 2 | 3 | 4 | 5 |
|---|---|---|---|---|
| Secobarbital | 200 ng/mL | 200 ng/mL | 1.00 | 100% |
| Amobarbital | 200 ng/mL | 310 ng/mL | 1.55 | 155% |

TABLE 3(a)-continued

| 1 | 2 | 3 | 4 | 5 |
|---|---|---|---|---|
| Butalbital | 200 ng/mL | 201 ng/mL | 1.00 | 100% |
| Pentobarbital | 200 ng/mL | 210 ng/mL | 1.05 | 105% |
| Phenobarbital | 200 ng/mL | 210 ng/mL | 1.05 | 105% |
| Talbutal | 200 ng/mL | 180 ng/mL | 0.90 | 90% |

Each of the listed barbiturates is compared to secobarbital, which was used as a standard, and which was determined to have a cross-reactivity of 100% (a factor of 1.0). A factor of 1.0 indicates that the assay neither overestimated nor underestimated the actual concentration of the test compound which was originally added to the drug-free normal human urine. In other words, when 200 ng of secobarbital were added to drug-free normal human urine, approximately 200 ng of secobarbital were detected in the resulting urine sample. Thus, the closer the factor is to 1.0, the more accurate the assay is with respect to the particular test compound analyzed. This factor, and the percentage of cross-reactivity, both of which may be determined by taking a reading from the Abbott Laboratories' $TD_x$®0 Clinical Analyzer or $AD_x$® Drugs of Abuse System, may be employed to determine the amount of barbiturate which has actually been detected during the assay with the following mathematical formula:

$$\text{Factor} = \frac{\text{Concentration Determined}}{\text{Concentration Present}}$$

Examples: (1) $1.0 = \frac{200 \text{ ng/mL}}{200 \text{ ng/mL}}$ (Accurate)

(2) $0.83 = \frac{167 \text{ ng/mL}}{200 \text{ ng/mL}}$ (Underestimated)

(3) $1.33 = \frac{267 \text{ ng/mL}}{200 \text{ ng/mL}}$ (Overestimated)

The percent cross-reactivity value presented in column five was obtained by the following mathematical formula:

$$\text{Percent Cross-Reactivity} = 100 \times \frac{\text{Concentration of Test Compound Detected in the Resulting Human Urine}}{\text{Concentration of Test Compound Added to Normal Drug-Free Human Urine}}$$

However, for the most preferred embodiment of the assay of the present invention, representative cross-reactivity data for the commonly-used barbiturates wherein the tracer has the structure shown in FIG. 30 and the antibodies have been raised against an immunogen having the structure shown in FIG. 29 are shown in Table 3(b) below.

TABLE 3(b)

| 1 | 2 | 3 | 4 | 5 |
|---|---|---|---|---|
| Secobarbital | 200 ng/mL | 200 ng/mL | 1.00 | 100% |
| Amobarbital | 200 ng/mL | 85 ng/mL | 0.43 | 43% |
| Aprobarbital | 200 ng/mL | 123 ng/mL | 0.62 | 62% |
| Butalbital | 200 ng/mL | 227 ng/mL | 1.13 | 113% |
| Butabarbital | 200 ng/mL | 489 ng/mL | 2.24 | 224% |
| Brallobarbital | 200 ng/mL | 188 ng/mL | 0.94 | 94% |
| Pentobarbital | 200 ng/mL | 129 ng/mL | 0.65 | 65% |
| Phenobarbital | 200 ng/mL | 140 ng/mL | 0.70 | 70% |
| Talbutal | 200 ng/mL | 531 ng/mL | 2.65 | 265% |

Another advantage of the present invention is the low cross-reactivity with nonbarbiturate compounds. Cross-reactivity was also tested with compounds that have similar chemical structures to the commonly-used barbiturates. Representative cross-reactivity data which indicate a low cross-reactivity for the compounds that have similar chemical structures to the commonly-used barbiturates are shown in Tables 4(a) (for a tracer having the structure shown in FIG. 5) and 4(b) (for a tracer having the structure shown in FIG. 30) below. The five columns in Tables 4(a) and 4(b) indicate the same information as is described above for Table 3(a).

TABLE 4(a)

| 1 | 2 | 3 | 4 | 5 |
|---|---|---|---|---|
| Glutethimide | 10 µg/mL | 180 ng/mL | 0.018 | 1.80% |
|  | 1 µg/mL | ND |  |  |
| p-Hydroxy phenytoin | 100 µg/mL | 1200 ng/mL | 0.012 | 1.20% |
|  | 10 µg/mL | 340 ng/mL | 0.034 | 3.40% |
|  | 1 µg/mL | ND |  |  |
| Phenytoin | 100 µg/mL | 1020 ng/mL | 0.0102 | 1.02% |
|  | 10 µg/mL | 320 ng/mL | 0.032 | 3.20% |
|  | 1 µg/mL | ND |  |  |
| Primidone | 100 µg/mL | 320 ng/mL | 0.0032 | 0.32% |
|  | 10 µg/mL | 90 ng/mL | 0.009 | 0.90% |
|  | 1 µg/mL | ND |  |  |
| Ibuprofen | 100 µg/mL | 70 ng/mL | 0.0007 | 0.07% |
|  | 10 µg/mL | ND |  |  |
|  | 1 µg/mL | ND |  |  |
| OH-Ibuprofen | 1000 µg/mL | 60 ng/mL | 0.00006 | 0.006% |
|  | 100 µg/mL | ND |  |  |
|  | 10 µg/mL | ND |  |  |
|  | 1 µg/mL | ND |  |  |
| Fenoprofen | 430 µg/mL | 290 ng/mL | 0.00067 | 0.067% |
|  | 215 µg/mL | 180 ng/mL | 0.00084 | 0.084% |
| Naproxen | 100 µg/mL | 70 ng/mL | 0.0007 | 0.07% |
|  | 10 µg/mL | ND |  |  |

ND = None detected: Concentration less than the sensitivity of the assay (60 ng/mL).

TABLE 4(b)

| 1 | 2 | 3 | 4 | 5 |
|---|---|---|---|---|
| Glutethimide | 10 µg/mL | 480 ng/mL | 0.048 | 4.80% |
|  | 1 µg/mL | 89 ng/mL | 0.089 | 8.90% |
| p-Hydroxy phenytoin | 500 µg/mL | 218 ng/mL | 0.00004 | 0.04% |
|  | 100 µg/mL | 101 ng/mL | 0.00010 | 0.10% |
|  | 10 µg/mL | ND |  |  |
| Primidone | 100 µg/mL | 195 ng/mL | 0.00019 | 0.19% |
|  | 10 µg/mL | ND |  |  |
| Amino-glutethimide | 100 µg/mL | 412 ng/mL | 0.00041 | 0.41% |
|  | 10 µg/mL | 117 ng/mL | 0.00117 | 1.17% |
|  | 1 µg/mL | ND |  |  |

Representative cross reactivity data which indicates a low cross reactivity to compounds which have similar chemical structures to several of the common-used barbiturates, as well as to other barbiturates and to barbiturate-like structures, are shown in Table 5 below for an immunogen having the structure shown in FIG. 29 and for tracers having the structures shown in FIGS. 30 and 31.

TABLE 5

| | | FIG. 31 | | FIG. 30 | |
|---|---|---|---|---|---|
| Compound | Conc. Added (ng/mL) | Conc. Found (ng/mL) | % CR | Conc. Found (ng/mL) | % CR |
| Alphenal | 1200 | HI | >167 | 1130 | 94 |
| Amobarbital | 1200 | 870 | 73 | 490 | 41 |
| Aprobarbital | 1200 | 1670 | 139 | 920 | 77 |
| Brallobarbital | 1200 | 1910 | 159 | 1400 | 117 |
| Butabarbital | 1200 | HI | >167 | HI | >167 |
| Butalbital | 1200 | HI | >167 | 2000 | 167 |
| Butobarbital | 1200 | NA | NA | 580 | 48 |
| Cyclopentobarbital | 1200 | HI | >167 | HI | >167 |
| Pentobarbital | 1200 | 770 | 64 | 740 | 62 |
| Phenobarbital | 1200 | 1280 | 107 | 740 | 62 |
| Talbutal | 1200 | HI | >167 | HI | >167 |
| UNDESIRABLE COMPOUNDS FOR CROSSREACTIVITY | | | | | |
| Phenytoin | 100 | 90 | 0.09 | 40 | 0.04 |
| HPPH (Phenytoin metabolite) | 500 | 290 | 0.058 | 200 | 0.001 |
| Ibuprofen | 1000 | 50 | 0.005 | 20 | 0.002 |
| Naproxen | 100 | 20 | 0.02 | 20 | 0.02 |
| Fenoprofen | 200 | 40 | 0.02 | 30 | 0.015 |
| Glutethimide | 10 | 470 | 4.70 | 470 | 4.70 |
| Primidone | 100 | 240 | 0.24 | 180 | 0.18 |

NA = Not Available

In addition, the compounds presented in Table 6(a) showed cross-reactivity results for a tracer having the structure shown in FIG. 5 less than 0.06 ug/mL when tested at 1.0, 10.0 and 100.0 ug/mL.

TABLE 6(a)

| | | |
|---|---|---|
| Acetaminophen | Acetylsalicylic Acid | Alprazolam |
| Aminopyrine | Amitriptyline | Amoxicillin |
| d,1-Amphetamine | Ampicillin | Antabuse |
| Apomorphine | Atenolol | Atrophine |
| Benzocaine | Benzoylecgonine | Caffeine |
| Calcium Hypochlorite | Carbamazepine | Cephalexin |
| Chlordiazepoxide | Chloroquine | Chlorpheniramine |
| Chlorpromazine | | Chlorpropamide |
| Cimetidine | Clonidine | Cocaine |
| Codeine | Cyclizine | Dextromethorphan |
| Diazepam | Diflunisal | Digoxin |
| Ecgonine | Ephedrine | Epinephrine |
| Erythromycin | Estriol | Estrone-3-sulfate |
| Flurazepam | Furosemide | Gentisic Acid |
| Guaiacol Glyceryl Ether | Hydrochlorothiazide | 4-OH-PIP-Phencyclidine |
| Imipramine | Indomethacin | Levothyroxine |
| Loxapine | Meperidine | Mephenytoin |
| Meprobamate | Methadone | d,1-Methamphetamine |
| Methaqualone | Methyldopa | Methyprylon |
| Metoprolol | Morphine | Naficillin |
| Naloxone | Nalorphine | Naltrexone |
| Nicotine | Nicotinic Acid | Nifedipine |
| Norethindrone | Oxazepam | Penicillin |
| Phencyclidine | Phenmetrazine | Phenothiazine |
| Phentermine | Phenylbutazone | Phenylpropanolamine |
| Piroxicam | Potassium Chloride | Promethazine |
| Promazine | Propoxyphene | Propranolol |
| Quinine | Quinine Bisulfate | Quinidine |
| Terbutaline | Tetracycline | Delta-8-tetrahydro-cannabinol-carboxylic acid |
| Delta-9-tetrahydro-cannabinol- | | |

TABLE 6(a)-continued

| | | |
|---|---|---|
| carboxylic acid | Tetrahydrozoline | Theophylline |
| Thiopropazate | Triamterene | Trifluoperazine |
| Trimethoprim | Uric Acid | Zomepirac |

The compounds presented in Table 6(b) showed cross-reactivity results for a tracer having the structure shown in FIG. 30 less than 60 ng/mL when tested at 100.0 ug/mL.

TABLE 6(b)

Acetaminophen
Acetopromazine
N-Acetyl-1-cysteine
Acetylsalicylic Acid
Alphaprodine
Alprazolam
Alprenolol
Amantadine
Aminopyrine
Amitriptyline
cis-10-OH-Amitriptyline
trans-10-OH-Amitriptyline
Amoxicillin
d,1-Amphetamine
p-OH-Amphetamine
Ampicillin
Anileridine
Antabuse
Apomorphine
Aprobarbital
Aspartame
Atenolol
Atropine
Azatadine
Beclomethasone
Benactyzine
Benzocaine
Benzioc Acid
Benzoylecgoinine
Benztropine
Benzylpenicillin
Bromocriptine Mesylate
Brompheniramine
Bupivacaine
Buspirone
Butorphanol
Caffeine
Calcium Hypochlorite
Carbamazepine
Carbamazepine-10,11-epoxide
Carisoprodol
Carphenazine
Cephalexin
Cephaloridine
Chloral Hydrate
Chloramphenicol
Chlordiazepoxide
Chloroquine
Chlorothiazide
Chlorpheniramine
Chlorpromazine
Chlorpropamide
Chlorzoxazone
Cholesterol
Cimetidine
Ciprofloxacin
Clemastine
Clindamycin
Clomipramine
Clonidine
Cocaine
Codeine
Cortisone
β-Cortol
Cyclazocine
Cyclizine
Cyclobenzaprine TABLE 6(b)-continued Cyclozocine
Cyproheptadine
Deoxycorticosterone
Desipramine
Dextromethorphan
Diacetylmorphine
Diazepam
Dibenzepin
Dibucaine
Diethylpropion
Diflunisal
Digitoxin
Digoxin
Dihydrocodeine
Dihydromorphine
10,11-Dihydroxy-carbamazepine
Diltiazem
Diphenhydramine
Diphenoxylate
Diphenylhydantoin
Dipyridamole
Dopamine
Dothiepin
Doxepin
Doxylamine
Ecgonine
Ephedrine
Epinephrine
Erythromycin
Estradiol
Estriol
Estrone-3-sulfate
Ethambutol
Ethinamate
4-Ethyl-2,5-dimethoxy-amphetamine (DOET)
Ethylmorphine
Fencamfamine
Fenfluramine
*Fenoprofen
Fentanyl
Flufenamic Acid
Fluoxetine
Fluphenazine
Flurazepam
Flurbiproten
Furosemide
Gentisic Acid
Glycopyrrolate
Guaiacol Glyceryl Ether
Haloperidol
Hippuric Acid
Histamine
Hydralazine
Hydrochlorothiazide
Hydrocodone
Hydrocortisone
Hydromorphone
5-hydroxyindole-3-acetic Acid
5-Hydroxyindole-2-carboxylic Acid
Hydroxyzine
**Ibuprofen
**COOH-Ibuprofen
**OH-Ibuprofen
Iminostilbene
Imipramine
Indole-3-acetic Acid
Indole-3-butyric Acid
Indomethacin
Iproniazid
Isoproterenol
Isoxsuprine
Ketamine
Ketoprofen
Labetalol
Levallorphan
Levorphanol
Levothyroxine
Lidocaine
Loperamide TABLE 6(b)-continued Loratadine
Lorazepam
Loxapine
LSD
Maprotiline
Mefenamic Acid
Melanin
Meperidine
Mephenytoin
Mepivacaine
Meprobamate
Mescaline
Methadone
Methadone Primary Metabolite
d-Methamphetamine
d,l-Methamphetamine
Methapyrilene
Methaqualone
Methocarbamol
Methotrimeprazine
Methoxyphenamine
Methoxypromazine
Methsuximide
4-Methyl-2,5-dimethoxy-amphetamine (DOM)
3,4-Methylenedioxy-amphetamine (MDA)
3,4-Methylenedioxy-N-ethyl-amphetamine (MDE)
3,4-Methylenedioxy-methamphetamine (MDMA)
Methylphenidate
Methyprylon
Metoclopramide
Metoprolol
Metronidazole
6-Monoacetylmorphine
Monoethylglycinexylidide (MEGX)
Morphine
Morphine-3β-D-glucuronide
Nafcillin
Nalbuphine
Nalorphine
Naloxone
Naltrexone
Naphazoline
*Naproxen
Niacinamide
Nicotine
Nicontinic Acid
Nifedipine
p-Nitrophenol
Nomifensine
Norchloriazepoxide
N-Norcodeine
Nordoxepin
Norethindrone
N-Normorphine
N-Noroxymorphone
N-Norpropoxyphene
Nortropoxyphene
Nortriptyline
cis-10-OH-Nortriptyline
trans-10-OH-Nortriptyline
Nylidrin
Octopamine
Opipramol
Orotic Acid
Orphenadrine
Oxazepam
Oxycodone
Oxymetazoline
Oxmorphone
Oxyphenbutazone
Parnate
Pemoline
Penicillin G
Pentazocine
Phenacetin
Phencyclidine
4-OH pip Phencyclidine
1-Phencyclohexylamine
Phendimetrazine

TABLE 6(b)-continued

Phenelzine
Phenethylamine
Phenformin
Pheniramine
Phenmetrazine
Phenothiazine
Phentermine
Phenylbutazone
Phenylpropanolamine
Phenyltoloxamine
Phenytoin
Picenadol
Piperacetazine
1-Piperidinocyclohexyphene
Piroxicam
Potassium Chloride
Prazosin
Prednisolone
Prednisone
Pregnenolone
Prilocaine
Probenecid
Procainamide
Procaine
Prochlorperazine
Progesterone
Prolintane
Promazine
Promethazine
Propoxyphene
Propranolol
Propylhexedrine
Protriptyline
Pseudoephedrine
Pyrilamine
Quinidine
Quinine
Ranitidine
Salicylic Acid
Scopolamine
Serotonin
Strychnine
Sudoxicam
Sulfamethazine
Sulfamethoxazole
Sulfathiazole
Sulindac
Terbutaline
Testosterone
Tetracaine
Tetracycline
***11-Nor-delta-9-tetrahydrocannabinol-carboxylic-9-acid
Tetrahydrocortisone
Tetrahydrozoline
Thebaine
Thenyldiamine
Theophylline
Thiopropazate
Thioridazine
Thiothixene
Tolbutamide
Trazodone
Triamterene
Trifluoperazine
Triflupromazine
Trihexphenidyl
Trimethoprim
Trimipramine
Tripelennamine
Triprolidine
Tropic Acid
Tropine
Tryptamine
Tyramine

TABLE 6(b)-continued

Uric Acid
Warfarin
Zomepirac

*- Tested at 500 ug/mL
**- Tested at 1000 ug/mL
***- Tested at 10 ug/mL

An additional advantage of the method of the present invention is the lack of interference by compounds commonly found in urine. The assay of the present invention (tracer-structure shown in FIG. 5; antibodies generated against an immunogen having the structure shown in FIG. 28) resulted in less than 10% error in detecting added drug (compounds at the concentrations listed in Table 7, compounds which are commonly found in urine, and which have the capability of interfering with all immunoassays such as that of the present invention and, thus, potentially render the results of the assay inaccurate) when drugs were added to normal barbiturate-containing human urine. The most preferred embodiment of the assay of the present invention (tracer-structure shown in FIG. 30; antibodies-generated against an immunogen having the structure shown in FIG. 29) demonstrated a similar lack of interference by compounds commonly found in urine.

TABLE 7

| Compound | Concentration Tested |
|---|---|
| Acetone | 1.0 g/dL |
| Ascorbic Acid | 1.5 g/dL |
| Bilirubin | 0.250 mg/dL |
| Creatinine | 500.0 mg/dL |
| Ethanol | 1.0 g/dL |
| Glucose | 2.0 g/dL |
| NaCl | 6.0 g/dL |
| Oxalic Acid | 100.0 mg/dL |
| Protein | 0.05 g/dL |
| Riboflavin | 7.5 mg/dL |
| Lysed Red Blood Cells (Hgb Concentration) | 115.0 mg/dL |
| Urea | 6.0 g/dL |

An additional advantage of the method of the present invention is the low carryover which occurs from drugs between samples (from one sample to another). Carryover was determined with the following mathematical formula after assaying a secobarbital solution in normal human urine at 1195 ug/mL using a tracer having the structure shown in FIG. 5 and antibodies generated against an immunogen having the structure shown in FIG. 28 on the Abbott Laboratories' $AD_x$® Drugs of Abuse System followed by a sample of drug-free normal human urine on the same carousel of the Clinical Analyzer:

$$\text{Percent Carryover} = 100 \times \frac{\text{Measured Concentration of Secobarbital Found in the Drug-Free Urine}}{\text{Concentration of the Secobardital Solution}}$$

The carryover was determined to be less than 0.02%. When the carryover was similarly determined after assaying a similar solution in normal human urine at 500 ug/mL with a tracer having the structure shown in FIG. 30 and antibodies generated against an immunogen having the structure shown in FIG. 29, the carryover was determined to be less than 0.03%.

Yet, a further advantage of the method of the present invention is the precision of drug determination. The precision of the assay of the present invention employing a tracer having the structure shown in FIG. 5 and antibodies generated against an immunogen having the structure shown in FIG. 28 was also determined to be quite favorable. Reproducibility of the assay was determined over thirteen different runs of the assay during a period of two weeks by assaying four replicates each of secobarbital in normal human urine at 0.4, 0.6, and 1.0 ug/mL. The concentration of each of the replicates was determined from a standard curve run in singles on the first day of the study. Results from these studies typically yielded coefficients of variation of less than 6%. Representative data are presented in Table 8(a) below.

TABLE 8(a)

|  | Concentration (ug/mL) | | |
| --- | --- | --- | --- |
| Target Value (n = 52) | 0.4 | 0.6 | 1.00 |
| Mean | 0.41 | 0.60 | 1.00 |
| Standard Deviation Within Run | 0.02 | 0.02 | 0.03 |
| Coefficient of Variation Within Run (%) | 5.10 | 2.95 | 3.05 |
| Standard Deviation Between Run | 0.02 | 0.02 | 0.04 |
| Coefficient of Variation Between Run (%) | 5.28 | 3.48 | 3.83 |

Reproducibility of the assay employing a tracer having the structure shown in FIG. 30 and antibodies generated against an immunogen having the structures shown in FIG. 29 was determined over ten different runs of the assay during a period of two weeks by assaying five replicates each of secobarbital in normal human urine at 300, 800 and 1500 ng/mL. Results from these studies typically yielded coefficients of variation of less than 7%. Representative data are presented in Table 8(b) below.

TABLE 8(b)

|  | Concentration (ug/mL) | | |
| --- | --- | --- | --- |
| Target Value (n = 50) | 300 | 800 | 1500 |
| Mean | 286.31 | 804.77 | 1448.04 |
| Standard Deviation Within Run | 8.41 | 37.88 | 37.99 |
| Coefficient of Variation Within Run (%) | 2.94 | 4.71 | 2.62 |
| Standard Deviation Between Run | 17.73 | 40.83 | 45.12 |
| Coefficient of Variation Between Run (%) | 6.19 | 5.07 | 3.12 |

In addition, precision was determined by running the Abbott Laboratories' $AD_x$® Systems Multiconstituent Low Control for Abused Drug Assays in replicates of three in both combination and Panel modes. Representative data are presented in Tables 9(a) (tracer-structure shown in FIG. 5; antibodies-generated against an immunogen having the structure shown in FIG. 28) and 9(b) (tracer-structure shown in FIG. 30; antibodies-generated against an immunogen having the structure shown in FIG. 29) below.

TABLE 9(a)

|  | Concentration (ug/mL) |
| --- | --- |
| Target Value (n = 54) | 0.6 |
| Mean | 0.59 |
| Standard Deviation Within Run | 0.03 |
| Coefficient of Variation Within Run (%) | 4.51 |
| Standard Deviation Between Run | 0.03 |
| Coefficient of Variation Between Run (%) | 4.73 |

TABLE 9(b)

|  | Concentration (ug/mL) |
| --- | --- |
| Target Value (n = 54) | 300 |
| Mean | 273 |
| Standard Deviation Within Run | 16.88 |
| Coefficient of Variation Within Run (%) | 6.18 |
| Standard Deviation Between Run | 16.90 |
| Coefficient of Variation Between Run (%) | 6.19 |

A further advantage of the method of the present invention is the accuracy of the assay. The accuracy of the recovery of the assay of the present invention was determined by preparing two sets of calibrators by adding known quantities of secobarbital to normal human urine and diluent buffer to levels of 0.2, 0.4, 0.7, 1.2 and 2.0 ug/mL for Table 10(a) and to levels of 200, 400, 700, 1200 and 2000 ng/mL for Table 10(b). A calibration was run with urine calibrators and both sets of calibrators were assayed on the Abbott Laboratories' $TD_x$® Clinical Analyzer relative to this calibration. The percent recovery was determined according to the following mathematical formula:

$$\text{Percent Recovery} = 100 \times \frac{\text{Measured Concentration in Urine}}{\text{Measured Concentration in Buffer}}$$

Representative data are presented in Table 10(a) (tracer-structure shown in FIG. 5; antibodies-generated against an immunogen having the structure shown in FIG. 28) and 10(b) (tracer-structure shown in FIG. 30; antibodies-generated against an immunogen having the structure shown in FIG. 29) below.

TABLE 10(a)

| Target Concentration (ug/mL) | Concentration in Buffer (ug/mL) | Concentration in Urine Percent (ug/mL) | Recovery |
| --- | --- | --- | --- |
| 0.2 | 0.18 | 0.20 | 111.1 |
| 0.4 | 0.38 | 0.41 | 107.9 |
| 0.7 | 0.69 | 0.72 | 104.4 |
| 1.2 | 1.16 | 1.22 | 105.2 |
| 2.0 | 1.96 | 2.02 | 103.1 |
| Average Recovery = 106.3 ± 3.2% | | | |

TABLE 10(b)

| Target Concentration (ug/mL) | Concentration in Buffer (ug/mL) | Concentration in Urine Percent (ug/mL) | Recovery |
| --- | --- | --- | --- |
| 200 | 185 | 200 | 92.5 |
| 400 | 398 | 412 | 96.6 |
| 700 | 699 | 692 | 101.0 |
| 1200 | 1231 | 1256 | 98.0 |
| 2000 | 2047 | 2068 | 99.0 |
| Average Recovery = 97.1 ± 2.5% | | | |

The assay of the present invention was also compared to other methods for the detection of barbiturates, such as gas chromatography/mass spectroscopy, radioimmunoassay (RIA) and EMIT®, by assaying drug-free urine specimens and urine specimens containing barbiturates and barbiturate metabolites. Representative data are presented below in Tables 11(a) (tracer-structure shown in FIG. 5; antibodies-generated against an immunogen having the structure shown in FIG. 28), 11(b) (tracer-structure shown in FIG. 30; antibodies-generated against an immunogen having the structure shown in FIG. 29 compared with EMIT®), and 11(c) (tracer-structure shown in FIG. 30; antibodies-generated against an immunogen having the structure shown in FIG. 29 compared with RIA) below.

TABLE 11(a)

| Sample Type | Number of Samples | Present Invention (Pos/Neg) | Testing Methodology GC/MS (Pos/Neg) | EMIT®/ d.a.u.™ (Pos/Neg) |
|---|---|---|---|---|
| ≧0.50 ug/mL | 149 | 149/0 | 149/0 | 149/0 |

TABLE 11(b)

| | N | TDx® POS/NEG | ADx® POS/NEG | Emit® POS/NEG | GC/MS POS/NEG |
|---|---|---|---|---|---|
| <200 ng/mL | 128 | 0/128 | 0/128 | 0/128 | $2^{1,2}$/0 |
| ≧200 ng/mL | 101 | 101/0 | 101/0 | 100/1 | $99/2^{3,4}$ |

| SAMPLE NUMBER | TDx® ng/mL | ADx® ng/mL | EMIT® POS/NEG | GC/MS ng/mL | COMPOUNDS IDENTIFIED |
|---|---|---|---|---|---|
| 1 | 110.62 | 73 | POS | 226 | Phenobarbital |
| 2 | 156.69 | 150 | NEG | 230 | Phenobarbital |
| 3 | 1911.93 | HIGH | POS | 0 | Glutethimide |
| 4 | 245.13 | 283 | NEG | 193 | Phenobarbltal |

TABLE 11(c)

| | N | TDx® POS/NEG | ADx® POS/NEG | Emit® POS/NEG | GC/MS POS/NEG |
|---|---|---|---|---|---|
| <200 ng/mL | 108 | 0/108 | $1^1$/128 | 0/108 | $2^{1,2}$/9 |
| ≧200 ng/mL | 91 | 91/0 | 91/0 | 78/13 | 97 NT 91/0 |

| SAMPLE NUMBER | TDx® ng/mL | ADx® ng/mL | RIA POS/NEG | GC/MS ng/mL | COMPOUNDS IDENTIFIED |
|---|---|---|---|---|---|
| 1 | 184.13 | 203 | NEG | 202 | Phenobarbital |
| 2 | 125.00 | 127 | NEG | 207 | Phenobarbital |

While the present invention has been described herein with some particularity, those of skill in the art will recognize numerous modifications and variations which remain within the spirit of the invention. These modifications and variations are within the scope of the invention as described and claimed herein.

We claim:

1. A process for determining the presence or amount of barbiturates in biological fluids comprising the steps of:

(a) contacting a sample with a barbiturate antiserum, said barbiturate antiserum containing polyclonal antibodies which have been raised against an immunogen of the following formula:

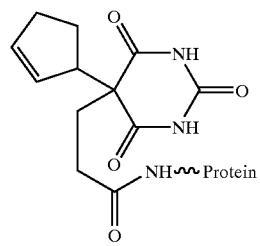

and with a tracer compound of the following formula:

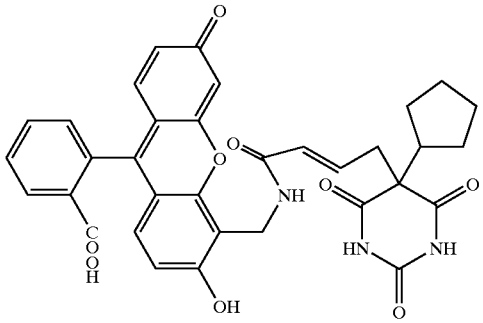

(b) passing plane polarized light through the resulting solution from step (a) to obtain a fluorescence polarization response; and
   (c) detecting the fluorescence polarization response of the solution of step (b) as a measure of the presence or amount of barbiturate in the sample.

2. A reagent kit for determining the presence or amount of barbituates in biological fluids which comprises:

(a) a tracer of the formula:

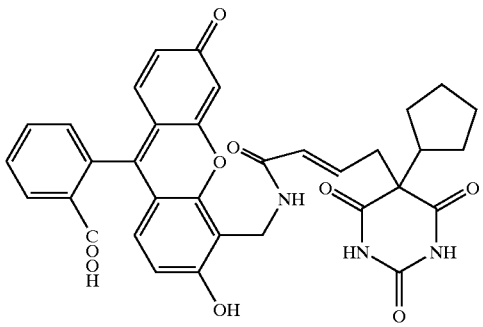

and (b) a polyclonal antibody which has been raised against an immunogen of the formula:

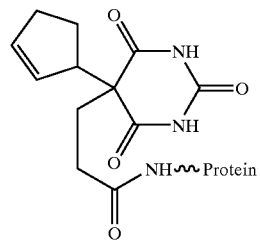

* * * * *